US009724083B2

(12) United States Patent
Quadri et al.

(10) Patent No.: US 9,724,083 B2
(45) Date of Patent: Aug. 8, 2017

(54) SYSTEMS AND METHODS FOR SEALING OPENINGS IN AN ANATOMICAL WALL

(71) Applicant: Edwards Lifesciences CardiAQ LLC, Irvine, CA (US)

(72) Inventors: Arshad Quadri, West Hartford, CT (US); J. Brent Ratz, Winchester, MA (US); Glen T. Rabito, Lake Forest, CA (US); Garrett Dallas Johnson, Costa Mesa, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 262 days.

(21) Appl. No.: 14/341,693

(22) Filed: Jul. 25, 2014

(65) Prior Publication Data

US 2015/0032153 A1 Jan. 29, 2015

Related U.S. Application Data

(60) Provisional application No. 61/859,038, filed on Jul. 26, 2013.

(51) Int. Cl.
| | |
|---|---|
| *A61B 17/00* | (2006.01) |
| *A61B 17/34* | (2006.01) |
| *A61M 1/10* | (2006.01) |

(52) U.S. Cl.
CPC ...... *A61B 17/0057* (2013.01); *A61B 17/3421* (2013.01); *A61B 17/3423* (2013.01);
(Continued)

(58) Field of Classification Search
CPC ...... A61B 17/0057; A61B 2017/00575; A61B 2017/00597; A61B 2017/00606;
(Continued)

(56) References Cited

U.S. PATENT DOCUMENTS

| | | |
|---|---|---|
| 1,306,391 A | 6/1919 | Romanoff |
| 3,312,237 A | 4/1967 | Mon et al. |

(Continued)

FOREIGN PATENT DOCUMENTS

| | | |
|---|---|---|
| CA | 2 827 556 A1 | 7/2012 |
| DE | 3128704 | 2/1983 |

(Continued)

OTHER PUBLICATIONS

International Search Report and Written Opinion for PCT/US2014/048281, mailed Nov. 18, 2014.

*Primary Examiner* — Elizabeth Houston
*Assistant Examiner* — Charles Wei
(74) *Attorney, Agent, or Firm* — Knobbe Martens Olson & Bear LLP

(57) ABSTRACT

Devices, systems and methods are described herein for sealing openings in an anatomical wall. A sealing system includes an elongate tubular support for delivery to an anatomical opening to be sealed, a cover of bio-compatible material covering a distal portion of the tubular support, and an anchor assembly, the anchor assembly being designed to secure the cover material to the opening. The anchor assembly can include a plurality of distal anchors and a plurality of proximal anchors, a button, ring or donut, and/or a C-clip. In some embodiments, the system further comprises a closure member for closing off an end of the cover material after removal of the tubular support.

17 Claims, 19 Drawing Sheets

(52) U.S. Cl.
CPC ............... *A61B 2017/0061* (2013.01); *A61B 2017/00243* (2013.01); *A61B 2017/00592* (2013.01); *A61B 2017/00597* (2013.01); *A61B 2017/00606* (2013.01); *A61B 2017/00623* (2013.01); *A61B 2017/00867* (2013.01); *A61B 2017/3425* (2013.01); *A61B 2017/3435* (2013.01); *A61M 1/1008* (2014.02)

(58) Field of Classification Search
CPC .... A61B 2017/3441; A61B 2017/3435; A61B 17/3421–17/3429; A61B 5/6865; A61M 39/0208; A61M 39/0247; A61M 2039/0223; A61M 2039/0261; A61F 5/442; A61F 5/443
USPC ................. 606/139, 149, 151, 153, 213–215
See application file for complete search history.

(56) References Cited

U.S. PATENT DOCUMENTS

| | | | |
|---|---|---|---|
| 4,477,930 A | 10/1984 | Totten et al. | |
| 4,693,257 A * | 9/1987 | Markham | A61B 10/0283 600/565 |
| 4,908,028 A | 3/1990 | Colon et al. | |
| 5,049,154 A | 9/1991 | Quadri | |
| 5,133,725 A | 7/1992 | Quadri | |
| 5,282,826 A | 2/1994 | Quadri | |
| 5,332,402 A | 7/1994 | Teitelbaum | |
| 5,397,355 A | 3/1995 | Marin | |
| 5,411,552 A | 5/1995 | Andersen et al. | |
| 5,439,446 A | 8/1995 | Barry | |
| 5,449,385 A | 9/1995 | Religa et al. | |
| 5,474,563 A | 12/1995 | Myler et al. | |
| 5,509,930 A | 4/1996 | Love | |
| 5,575,818 A | 11/1996 | Pinchuk | |
| 5,607,469 A | 3/1997 | Frey | |
| 5,713,952 A | 2/1998 | Vanney et al. | |
| 5,725,519 A | 3/1998 | Penner | |
| 5,807,398 A | 9/1998 | Shaknovich | |
| 5,810,873 A | 9/1998 | Morales | |
| 5,840,081 A | 11/1998 | Andersen et al. | |
| 5,853,395 A * | 12/1998 | Crook | A61B 17/3423 600/208 |
| 5,855,601 A | 1/1999 | Bessler et al. | |
| 5,876,437 A | 3/1999 | Vanney et al. | |
| 5,879,381 A | 3/1999 | Moriuch et al. | |
| 5,902,334 A | 5/1999 | Dwyer et al. | |
| 5,935,108 A | 8/1999 | Katoh | |
| 5,957,949 A | 9/1999 | Leonhardt et al. | |
| 5,992,000 A | 11/1999 | Humphrey et al. | |
| 6,004,328 A | 12/1999 | Solar | |
| 6,015,431 A | 1/2000 | Thornton et al. | |
| 6,053,940 A | 4/2000 | Wijay | |
| 6,113,612 A | 9/2000 | Swanson et al. | |
| 6,132,458 A | 10/2000 | Staehle et al. | |
| 6,159,237 A | 12/2000 | Alt | |
| 6,168,614 B1 | 1/2001 | Andersen et al. | |
| 6,168,616 B1 | 1/2001 | Brown, III | |
| 6,251,093 B1 | 6/2001 | Valley et al. | |
| 6,306,141 B1 | 10/2001 | Jervis | |
| 6,309,416 B1 | 10/2001 | Swanson et al. | |
| 6,336,938 B1 | 1/2002 | Kavteladze et al. | |
| 6,352,543 B1 | 3/2002 | Cole | |
| 6,358,277 B1 | 3/2002 | Duran | |
| 6,409,759 B1 | 6/2002 | Peredo | |
| 6,425,916 B1 | 7/2002 | Garrison et al. | |
| 6,440,163 B1 | 8/2002 | Swanson et al. | |
| 6,454,799 B1 | 9/2002 | Schreck | |
| 6,458,153 B1 | 10/2002 | Bailey et al. | |
| 6,475,237 B2 | 11/2002 | Drasler et al. | |
| 6,482,228 B1 | 11/2002 | Norred | |
| 6,485,467 B1 * | 11/2002 | Crook | A61B 17/3423 604/174 |
| 6,511,491 B2 | 1/2003 | Grudem et al. | |
| 6,517,573 B1 | 2/2003 | Pollock | |
| 6,527,800 B1 | 3/2003 | McGuckin, Jr. et al. | |
| 6,533,812 B2 | 3/2003 | Swanson et al. | |
| 6,582,462 B1 | 6/2003 | Andersen et al. | |
| 6,676,698 B2 | 1/2004 | McGuckin et al. | |
| 6,723,123 B1 | 4/2004 | Kazatchkov et al. | |
| 6,730,118 B2 | 5/2004 | Spenser et al. | |
| 6,733,523 B2 | 5/2004 | Shaolian et al. | |
| 6,767,362 B2 | 7/2004 | Schreck | |
| 6,780,200 B2 | 8/2004 | Jansen | |
| 6,790,229 B1 | 9/2004 | Berreklouw | |
| 6,790,230 B2 | 9/2004 | Beyersdorf et al. | |
| 6,830,584 B1 | 12/2004 | Seguin | |
| 6,858,034 B1 | 2/2005 | Hijlkema et al. | |
| 6,908,477 B2 | 6/2005 | McGuckin, Jr. et al. | |
| 6,908,481 B2 | 6/2005 | Cribier | |
| 6,926,732 B2 | 8/2005 | Derus et al. | |
| 6,936,058 B2 | 8/2005 | Forde et al. | |
| 6,960,219 B2 | 11/2005 | Grudem et al. | |
| 6,979,350 B2 | 12/2005 | Moll et al. | |
| 7,018,401 B1 | 3/2006 | Hyodoh et al. | |
| 7,018,406 B2 | 3/2006 | Seguin et al. | |
| 7,025,780 B2 | 4/2006 | Gabbay | |
| 7,044,134 B2 | 5/2006 | Khairkhahan et al. | |
| 7,044,966 B2 | 5/2006 | Svanidze et al. | |
| 7,147,661 B2 | 12/2006 | Chobotov et al. | |
| 7,153,322 B2 | 12/2006 | Alt | |
| 7,186,265 B2 | 3/2007 | Sharkawy et al. | |
| 7,201,772 B2 | 4/2007 | Schwammenthal et al. | |
| 7,232,449 B2 | 6/2007 | Sharkawy et al. | |
| 7,252,682 B2 | 8/2007 | Seguin | |
| 7,276,084 B2 | 10/2007 | Yang et al. | |
| 7,328,270 B1 | 2/2008 | Reents et al. | |
| 7,329,278 B2 | 2/2008 | Seguin et al. | |
| 7,374,571 B2 | 5/2008 | Pease et al. | |
| 7,381,219 B2 | 6/2008 | Salahieh et al. | |
| 7,422,602 B2 | 9/2008 | Grudem et al. | |
| 7,425,219 B2 | 9/2008 | Quadri | |
| 7,429,269 B2 | 9/2008 | Schwammenthal et al. | |
| 7,442,204 B2 | 10/2008 | Schwammenthal et al. | |
| 7,445,631 B2 | 11/2008 | Salahieh et al. | |
| 7,510,575 B2 | 3/2009 | Spenser et al. | |
| 7,534,261 B2 | 5/2009 | Friedman | |
| 7,585,321 B2 | 9/2009 | Cribier | |
| 7,628,805 B2 | 12/2009 | Spenser et al. | |
| 7,632,298 B2 | 12/2009 | Hijlkema et al. | |
| 7,748,389 B2 | 7/2010 | Salahieh et al. | |
| 7,771,463 B2 | 8/2010 | Ton et al. | |
| 7,771,472 B2 | 8/2010 | Hendricksen et al. | |
| 7,824,443 B2 | 11/2010 | Salahieh et al. | |
| 7,846,203 B2 | 12/2010 | Cribier | |
| 7,871,435 B2 | 1/2011 | Carpentier | |
| 7,959,672 B2 | 6/2011 | Salahieh et al. | |
| 7,972,378 B2 | 7/2011 | Tabor et al. | |
| 7,981,151 B2 | 7/2011 | Rowe | |
| 7,993,394 B2 | 8/2011 | Hariton et al. | |
| 8,016,870 B2 | 9/2011 | Chew et al. | |
| 8,016,877 B2 | 9/2011 | Seguin et al. | |
| 8,075,615 B2 | 12/2011 | Eberhardt et al. | |
| 8,092,520 B2 | 1/2012 | Quadri | |
| 8,167,926 B2 | 5/2012 | Hartley et al. | |
| 8,221,493 B2 | 7/2012 | Boyle et al. | |
| 8,236,045 B2 | 8/2012 | Benichou et al. | |
| 8,246,675 B2 | 8/2012 | Zegdi | |
| 8,252,051 B2 | 8/2012 | Chau et al. | |
| 8,337,541 B2 | 12/2012 | Quadri et al. | |
| 8,361,537 B2 | 1/2013 | Shanley | |
| 8,398,708 B2 | 3/2013 | Meiri et al. | |
| 8,403,983 B2 | 3/2013 | Quadri et al. | |
| 8,414,644 B2 | 4/2013 | Quadri et al. | |
| 8,414,645 B2 | 4/2013 | Dwork et al. | |
| 8,449,466 B2 | 5/2013 | Duhay et al. | |
| 8,449,599 B2 | 5/2013 | Chau et al. | |
| 8,470,023 B2 | 6/2013 | Eidenschink et al. | |
| 8,579,964 B2 | 11/2013 | Lane et al. | |
| 8,585,755 B2 | 11/2013 | Chau et al. | |
| 8,591,570 B2 | 11/2013 | Revuelta et al. | |
| 8,647,381 B2 | 2/2014 | Essinger et al. | |
| 8,652,203 B2 | 2/2014 | Quadri et al. | |

(56) References Cited

U.S. PATENT DOCUMENTS

| | | |
|---|---|---|
| 8,668,730 B2 | 3/2014 | McGuckin, Jr. et al. |
| 8,673,000 B2 | 3/2014 | Tabor et al. |
| 8,721,714 B2 | 5/2014 | Kelley |
| 8,728,154 B2 | 5/2014 | Alkhatib |
| 8,740,974 B2 | 6/2014 | Lambrecht et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,790,387 B2 | 7/2014 | Nguyen et al. |
| 8,795,356 B2 | 8/2014 | Quadri et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,894,702 B2 | 11/2014 | Quadri et al. |
| 9,474,545 B1* | 10/2016 | Kim ............... A61B 17/3423 |
| 2001/0047180 A1 | 11/2001 | Grudem et al. |
| 2001/0047200 A1 | 11/2001 | White |
| 2002/0022853 A1 | 2/2002 | Swanson et al. |
| 2002/0032481 A1 | 3/2002 | Gabbay |
| 2002/0045929 A1 | 4/2002 | Diaz |
| 2002/0055772 A1 | 5/2002 | McGuckin et al. |
| 2002/0077695 A1 | 6/2002 | Swanson et al. |
| 2002/0111619 A1 | 8/2002 | Keast et al. |
| 2002/0111647 A1 | 8/2002 | Khairkhahan et al. |
| 2003/0014104 A1 | 1/2003 | Cribier |
| 2003/0040681 A1* | 2/2003 | Ng ........................ A61B 10/02 |
| | | 600/562 |
| 2003/0040792 A1 | 2/2003 | Gabbay |
| 2003/0083679 A1 | 5/2003 | Grudem et al. |
| 2003/0109924 A1 | 6/2003 | Cribier |
| 2003/0187499 A1 | 10/2003 | Swanson et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093060 A1 | 5/2004 | Seguin et al. |
| 2004/0102842 A1 | 5/2004 | Jansen |
| 2004/0186561 A1 | 9/2004 | McGuckin, Jr. et al. |
| 2004/0210304 A1 | 10/2004 | Seguin et al. |
| 2004/0249433 A1 | 12/2004 | Freitag |
| 2005/0033398 A1 | 2/2005 | Seguin |
| 2005/0038470 A1 | 2/2005 | van der Burg et al. |
| 2005/0090887 A1 | 4/2005 | Pryor |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0182483 A1 | 8/2005 | Osborne et al. |
| 2005/0203616 A1 | 9/2005 | Cribier |
| 2005/0203618 A1 | 9/2005 | Sharkawy et al. |
| 2005/0234546 A1 | 10/2005 | Nugent et al. |
| 2005/0240204 A1 | 10/2005 | Grudem et al. |
| 2005/0251251 A1 | 11/2005 | Cribier |
| 2005/0283231 A1 | 12/2005 | Haug et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0106454 A1 | 5/2006 | Osborne et al. |
| 2006/0129235 A1 | 6/2006 | Seguin et al. |
| 2006/0149360 A1 | 7/2006 | Schwammenthal et al. |
| 2006/0195183 A1 | 8/2006 | Navia et al. |
| 2006/0212110 A1 | 9/2006 | Osborne et al. |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2007/0010876 A1 | 1/2007 | Salahieh et al. |
| 2007/0016286 A1 | 1/2007 | Herrmann et al. |
| 2007/0043435 A1 | 2/2007 | Seguin et al. |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0123798 A1* | 5/2007 | Rahamimov ...... A61B 1/00135 |
| | | 600/564 |
| 2007/0162107 A1 | 7/2007 | Haug et al. |
| 2007/0185559 A1 | 8/2007 | Shelso |
| 2007/0213813 A1 | 9/2007 | Von Segesser et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0270932 A1 | 11/2007 | Headley et al. |
| 2007/0270937 A1 | 11/2007 | Leanna |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071363 A1 | 3/2008 | Tuval et al. |
| 2008/0071369 A1 | 3/2008 | Tuval et al. |
| 2008/0125859 A1 | 5/2008 | Salahieh et al. |
| 2008/0133003 A1 | 6/2008 | Seguin |
| 2008/0140189 A1 | 6/2008 | Nguyen et al. |
| 2008/0147183 A1 | 6/2008 | Styrc |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243245 A1 | 10/2008 | Thambar et al. |
| 2008/0269878 A1 | 10/2008 | Lobbi |
| 2008/0275549 A1 | 11/2008 | Rowe |
| 2008/0275550 A1 | 11/2008 | Kheradvar et al. |
| 2009/0005863 A1 | 1/2009 | Goetz et al. |
| 2009/0012602 A1 | 1/2009 | Quadri |
| 2009/0054976 A1 | 2/2009 | Tuval et al. |
| 2009/0076585 A1 | 3/2009 | Hendriksen |
| 2009/0076598 A1 | 3/2009 | Salahieh et al. |
| 2009/0088836 A1 | 4/2009 | Bishop et al. |
| 2009/0099643 A1 | 4/2009 | Hyodoh et al. |
| 2009/0099653 A1 | 4/2009 | Suri et al. |
| 2009/0125104 A1 | 5/2009 | Hoffman |
| 2009/0132035 A1 | 5/2009 | Roth et al. |
| 2009/0132037 A1 | 5/2009 | Hoffman et al. |
| 2009/0138069 A1 | 5/2009 | Hoffman |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf et al. |
| 2009/0182407 A1 | 7/2009 | Leanna et al. |
| 2009/0192601 A1 | 7/2009 | Rafiee et al. |
| 2009/0216314 A1 | 8/2009 | Quadri |
| 2009/0248132 A1 | 10/2009 | Bloom et al. |
| 2009/0248133 A1 | 10/2009 | Bloom et al. |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0306768 A1 | 12/2009 | Quadri |
| 2010/0004740 A1 | 1/2010 | Sequin et al. |
| 2010/0036479 A1 | 2/2010 | Hill et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0114305 A1 | 5/2010 | Kang et al. |
| 2010/0121461 A1 | 5/2010 | Sobrino-Serrano et al. |
| 2010/0179647 A1 | 7/2010 | Carpenter et al. |
| 2010/0256723 A1 | 10/2010 | Murray |
| 2010/0262157 A1 | 10/2010 | Silver et al. |
| 2010/0274345 A1 | 10/2010 | Rust |
| 2010/0298931 A1 | 11/2010 | Quadri et al. |

(56) References Cited

U.S. PATENT DOCUMENTS

| | | |
|---|---|---|
| 2010/0312333 A1 | 12/2010 | Navia et al. |
| 2011/0022157 A1 | 1/2011 | Essinger et al. |
| 2011/0022164 A1 | 1/2011 | Quinn et al. |
| 2011/0022165 A1 | 1/2011 | Oba et al. |
| 2011/0022166 A1 | 1/2011 | Dahlgren et al. |
| 2011/0022169 A1 | 1/2011 | Ryan et al. |
| 2011/0029067 A1 | 2/2011 | McGuckin, Jr. et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0218619 A1 | 9/2011 | Benichou et al. |
| 2011/0224780 A1 | 9/2011 | Tabor et al. |
| 2011/0224785 A1 | 9/2011 | Hacohen |
| 2011/0313515 A1 | 12/2011 | Quadri et al. |
| 2011/0319989 A1 | 12/2011 | Lane et al. |
| 2012/0016411 A1 | 1/2012 | Tuval |
| 2012/0022639 A1 | 1/2012 | Hacohen et al. |
| 2012/0022640 A1 | 1/2012 | Gross et al. |
| 2012/0041550 A1 | 2/2012 | Salahieh et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0123529 A1 | 5/2012 | Levi et al. |
| 2012/0179239 A1 | 7/2012 | Quadri et al. |
| 2012/0215303 A1 | 8/2012 | Quadri et al. |
| 2012/0271398 A1 | 10/2012 | Essinger et al. |
| 2012/0283824 A1 | 11/2012 | Lutter et al. |
| 2012/0296418 A1 | 11/2012 | Bonyuet et al. |
| 2012/0303116 A1 | 11/2012 | Gorman, III et al. |
| 2013/0018458 A1 | 1/2013 | Yohanan et al. |
| 2013/0053950 A1 | 2/2013 | Rowe et al. |
| 2013/0110227 A1 | 5/2013 | Quadri et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0184811 A1 | 7/2013 | Rowe et al. |
| 2013/0184813 A1 | 7/2013 | Quadri et al. |
| 2013/0190861 A1 | 7/2013 | Chau et al. |
| 2013/0211508 A1 | 8/2013 | Lane et al. |
| 2013/0253635 A1 | 9/2013 | Straubinger et al. |
| 2013/0268066 A1 | 10/2013 | Rowe |
| 2013/0304200 A1 | 11/2013 | McLean et al. |
| 2013/0310926 A1 | 11/2013 | Hariton et al. |
| 2014/0005764 A1 | 1/2014 | Schroeder |
| 2014/0052237 A1 | 2/2014 | Lane et al. |
| 2014/0088694 A1 | 3/2014 | Rowe et al. |
| 2014/0100653 A1 | 4/2014 | Savage et al. |
| 2014/0155990 A1 | 6/2014 | Nyuli et al. |
| 2014/0172085 A1 | 6/2014 | Quadri et al. |
| 2014/0172086 A1 | 6/2014 | Quadri et al. |
| 2014/0214154 A1 | 7/2014 | Nguyen et al. |
| 2014/0214159 A1 | 7/2014 | Vidlund et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0257467 A1 | 9/2014 | Lane et al. |
| 2014/0277390 A1 | 9/2014 | Ratz et al. |
| 2014/0277422 A1 | 9/2014 | Ratz et al. |
| 2014/0277427 A1 | 9/2014 | Ratz et al. |
| 2014/0309731 A1 | 10/2014 | Quadri et al. |
| 2014/0343669 A1 | 11/2014 | Lane et al. |

FOREIGN PATENT DOCUMENTS

| | | |
|---|---|---|
| EP | 0 657 147 | 6/1995 |
| GB | 2 245 495 | 1/1992 |
| GB | 2 398 245 | 8/2004 |
| WO | WO 97/49355 | 12/1997 |
| WO | WO 00/53104 | 9/2000 |
| WO | WO 00/61034 | 10/2000 |
| WO | WO 01/35861 | 5/2001 |
| WO | WO 01/35870 | 5/2001 |
| WO | WO 03/011195 | 2/2003 |
| WO | WO 03/092554 | 11/2003 |
| WO | WO 2005/011534 | 2/2005 |
| WO | WO 2005/087140 | 9/2005 |
| WO | WO 2006/089236 | 8/2006 |
| WO | WO 2006/127765 | 11/2006 |
| WO | WO 2007/025028 | 3/2007 |
| WO | WO 2007/123658 | 11/2007 |
| WO | WO 2007/134290 | 11/2007 |
| WO | WO 2008/070797 | 6/2008 |
| WO | WO 2008/091515 | 7/2008 |
| WO | WO 2008/150529 | 12/2008 |
| WO | WO 2009/026563 | 2/2009 |
| WO | WO 2009/045331 | 4/2009 |
| WO | WO 2009/052188 | 4/2009 |
| WO | WO 2009/094500 | 7/2009 |
| WO | WO 2009/137359 | 11/2009 |
| WO | WO 2009/155561 | 12/2009 |
| WO | WO 2010/008549 | 1/2010 |
| WO | WO 2010/098857 | 9/2010 |
| WO | WO 2009/149462 | 1/2011 |
| WO | WO 2010/138853 | 2/2011 |
| WO | WO 2011/025945 | 3/2011 |
| WO | WO 2011/109801 | 1/2012 |
| WO | WO 2011/109813 | 1/2012 |
| WO | WO 2012/035279 | 3/2012 |
| WO | WO 2012/162228 | 11/2012 |
| WO | WO 2012/177942 | 12/2012 |
| WO | WO 2013/028387 | 2/2013 |
| WO | WO 2013/012801 | 4/2013 |
| WO | WO 2013/086413 | 6/2013 |

\* cited by examiner

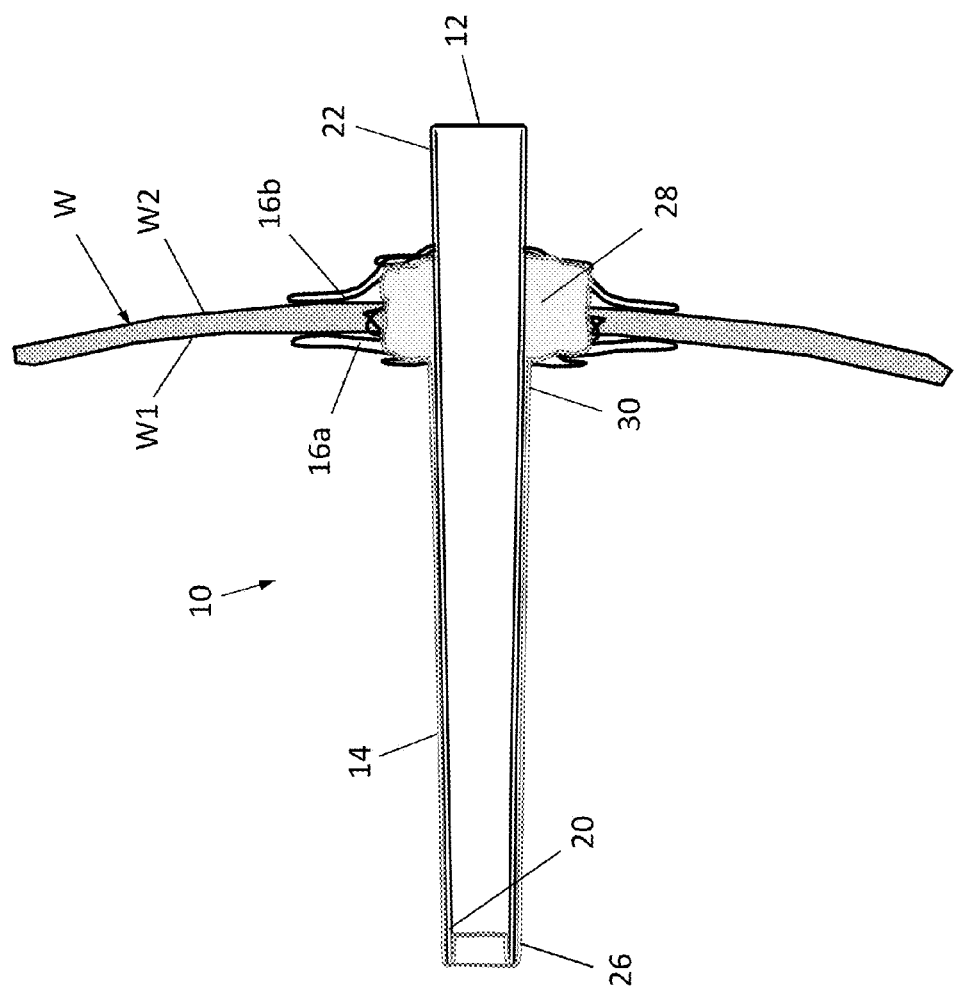

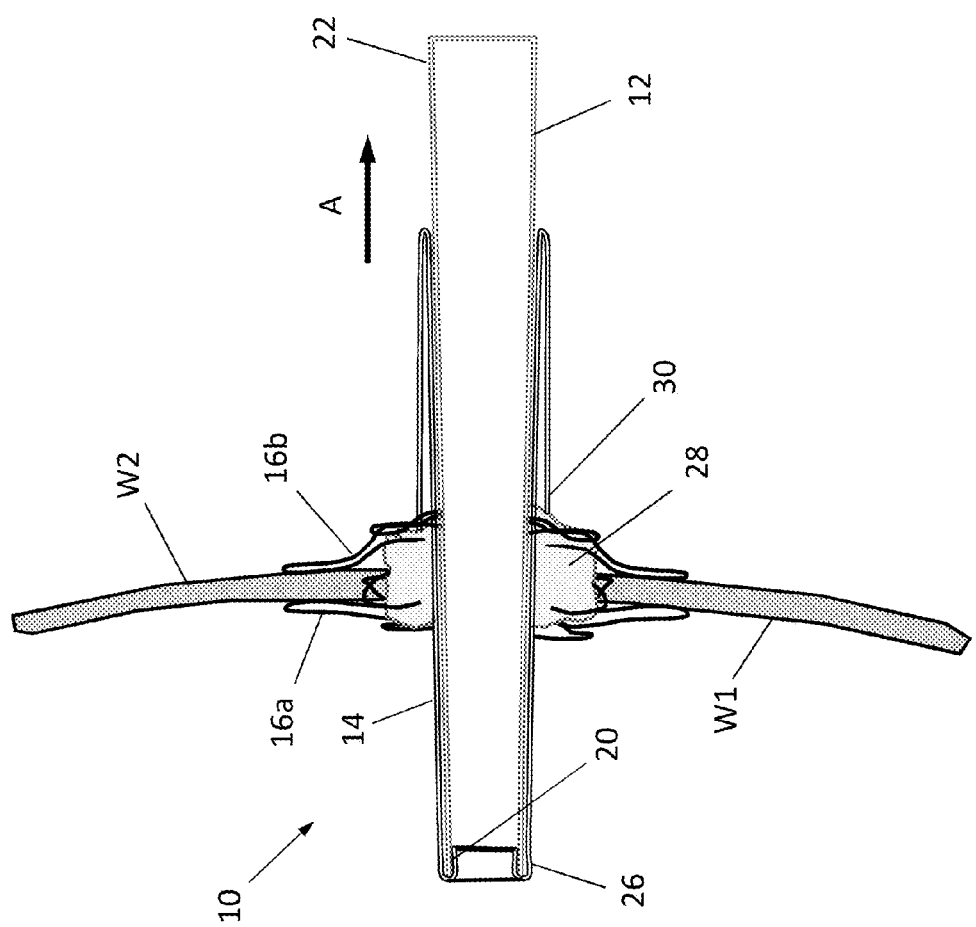

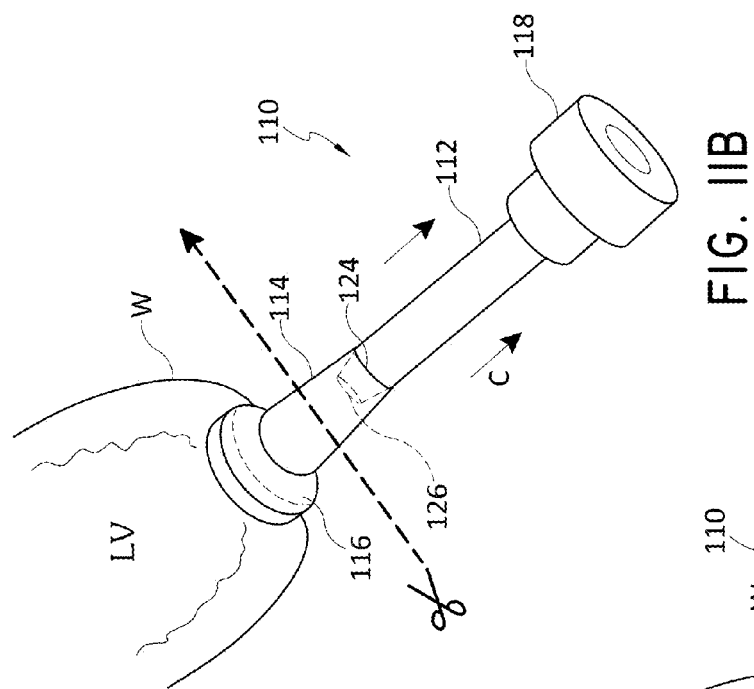
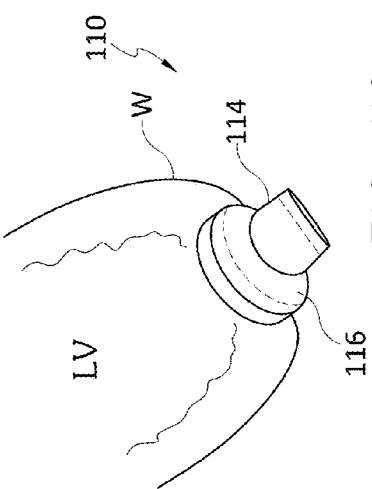
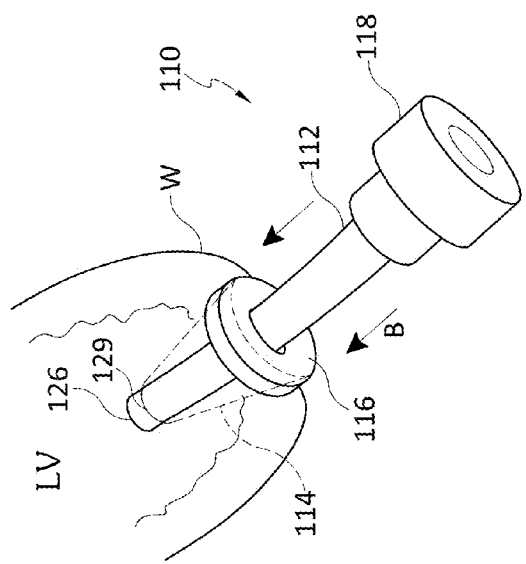
FIG. IIA
FIG. IIB
FIG. IIC

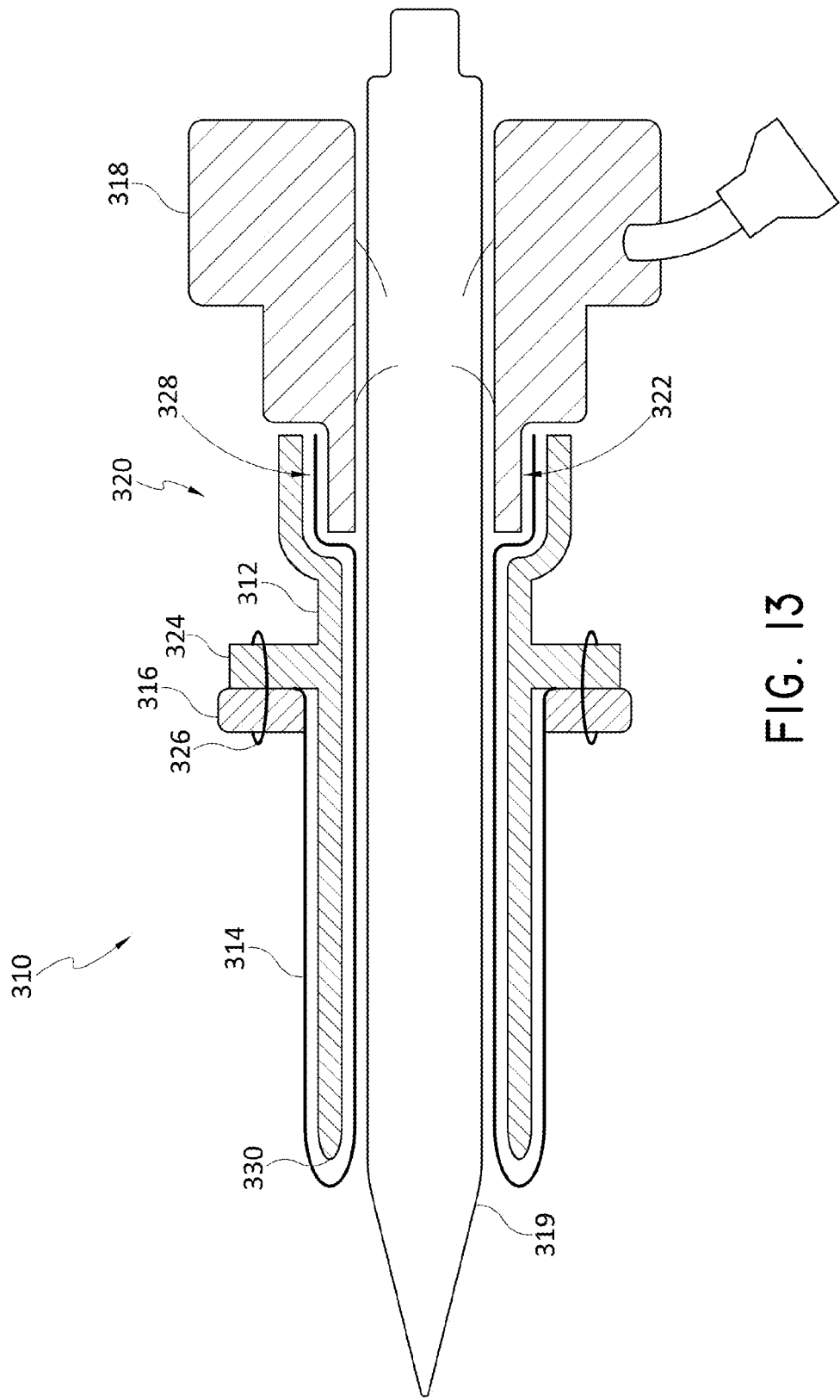

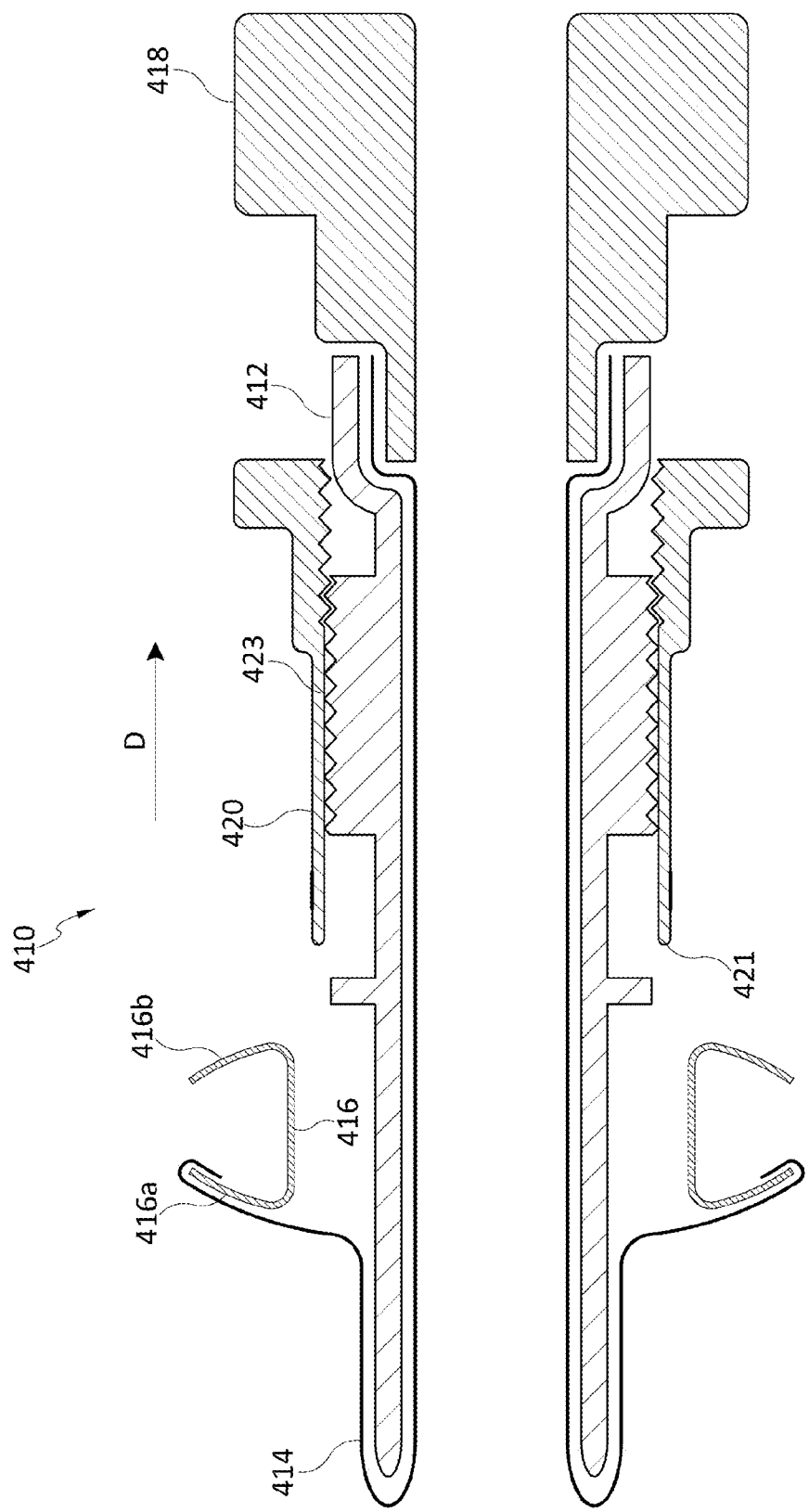

SYSTEMS AND METHODS FOR SEALING OPENINGS IN AN ANATOMICAL WALL

CROSS-REFERENCE TO RELATED APPLICATIONS

This application claims priority to U.S. Provisional App. No. 61/859,038 filed Jul. 26, 2013, titled PERCUTANEOUS PUNCTURE SEAL, which is hereby incorporated herein by reference in its entirety and is to be considered a part of this specification.

BACKGROUND

Field

The embodiments described herein relate generally to devices, systems and methods for sealing an opening in an anatomical wall. In particular, the embodiments described herein relate in some embodiments to devices, system and methods for sealing an opening or puncture formed in a heart wall during a surgical procedure, such as a percutaneous and/or transapical procedure.

Background

During a surgical procedure, including percutaneous procedures as well as semi-open and open surgical procedures, openings or punctures are often formed in anatomical walls of a patient's tissue in order to gain access to spaces beyond that anatomical wall. For example, during a transapical surgical procedure for replacing a heart valve, a puncture can be made proximate the apex of the heart in order to gain access to the ventricles or atria of the heart. One of the challenges that arise with the creation of such openings or punctures in anatomical walls is effectively and efficiently sealing of such openings or punctures. This can be particularly challenging when attempting to seal openings or punctures in anatomical walls which are subject to high pressures, such as cardiac tissue and tissue proximate the heart.

SUMMARY

Accordingly, there is a need for improved devices, systems and methods of sealing openings in an anatomical wall such as those formed during surgical procedures. The embodiments described herein relate to devices, systems and methods for sealing such openings and, in some embodiments, to sealing openings formed in a heart wall.

In one embodiment, the system comprises an elongate tubular support having a distal end and a proximal end, where the tubular support is configured for percutaneous delivery to the opening to be sealed. The embodiment preferably also comprises a cover of bio-compatible material configured to cover at least a portion of the tubular support from at least the distal end of the tubular support to a central portion of the tubular support, the cover material having a distal end configured to engage the distal end of the tubular support and a proximal end, the cover further comprising an anchor covering portion positioned proximate the proximal end of the cover. The embodiment further preferably comprises an anchor assembly comprising a plurality of distal anchors and a plurality of proximal anchors positioned proximal the central portion of the tubular support, the distal and proximal anchors sufficiently malleable and configured to be foldable against the tubular support when in a first delivery position, and to foldable radially outwardly away from the tubular support in a second wall engagement position. In some embodiments, the system further comprises a closure member for closing off an end of the cover material after removal of the tubular support.

With such a system, when the puncture seal system is deployed in-situ within an opening so that the distal anchors are positioned along the distal side of the opening wall and the proximal anchors are positioned along the proximal side of the opening wall, the anchors may be positioned in the wall engagement position to secure the seal system in place and permit actuation of the system to seal the opening by removing the tubular support and drawing the cover material inside-out from a distal-most position to a proximal-most position, wherein the opening is sealed using the anchor covering portion of the cover material in combination with the anchors.

In some embodiments, the system can include an elongate tubular support having a proximal end and a distal end, the tubular support designed to be delivered into an opening to be sealed. The system can include an anchor assembly designed to be secured to an anatomical wall adjacent the opening, wherein the elongate tubular support is positionable in a first position within the anchor assembly wherein the proximal end of the tubular support is proximal to the anchor assembly and the distal end of the tubular support is distal to the anchor assembly. The system can include a cover of bio-compatible material connected to the anchor assembly and designed to extend distally from the anchor assembly to cover at least a portion of the tubular support when the tubular support is in the first position. The tubular support can be moveable from the first position to a second position such that, in the second position the distal end of the tubular support is proximal to the anchor assembly, and movement of the tubular support from the first position to the second position draws the cover material inside-out such that the cover material extends proximally from the anchor assembly.

In some embodiments, the anchor assembly can include a plurality of proximal anchors and a plurality of distal anchors, the proximal and distal anchors being foldable towards the tubular support in a first delivery position and being expandable radially outwardly away from the tubular support in a second wall engagement position. In some embodiments, the cover can be connected to the distal anchors. In some embodiments, the cover can be connected to the proximal anchors. In some embodiments, the anchor assembly can include a C-clip. In some embodiments, the anchor assembly can include a button, donut or ring that is securable adjacent an opening in the anatomical wall.

In some embodiments, the cover can be connected to the tubular support at or near the distal end of the tubular support. In some embodiments, the cover can be connected to the tubular support at or near the proximal end of the tubular support. In some embodiments, when the tubular support is in its first position, the cover can extend to the distal end of the tubular support and be inverted to extend within a lumen of the tubular support. In some embodiments, the cover can be connected to the tubular support at or near a proximal end of the tubular support within the lumen. In some embodiments, the cover can be connected to the tubular support at or near the distal end of the tubular support within the lumen.

In some embodiments, a method can include the step of providing a sealing system having an elongate tubular support having a proximal end and a distal end, an anchor assembly provided over the elongate tubular support positioned between the proximal and distal ends, and a cover of bio-compatible material connected to the anchor assembly and extending distally therefrom to cover at least a portion of the tubular support. The method can include the step of positioning the tubular support within an opening within an anatomical wall such that the proximal end of the tubular support is proximal of the opening and the distal end of the tubular support is distal of the opening, wherein the cover covering at least a portion of the tubular support extends at least distally of the opening. The method can include the step of securing the anchor assembly to the anatomical wall adjacent the opening. The method can include the step of moving the tubular support in a proximal direction so as to draw the cover material inside-out from a distal-most position wherein the cover extends at least distally of the opening to a proximal-most position wherein the cover extends proximally of the opening. The method can include the step of sealing a portion of the cover extending proximally of the opening.

In some embodiments, the method can include the step of severing a portion of the cover extending proximally of the opening. In some embodiments, the opening within the anatomical wall can be formed by delivering the sealing system through the anatomical wall. In some embodiments, the step of delivering the sealing system can include the step of delivering a dilator through the anatomical wall simultaneously with the tubular support. In some embodiments, the step of securing the anchor assembly to the anatomical wall can include the step of expanding anchors on proximal and distal sides of the anatomical wall. In some embodiments, the step of securing the anchor assembly can include the step of suturing the anchor assembly to a proximal surface of the anatomical wall adjacent the opening. In some embodiments, the opening can be an opening in the heart. In some embodiments, the method can include the step of performing a procedure in the heart using one or more instruments delivered through a central lumen of the tubular support after securing the anchor assembly to the anatomical wall adjacent the opening and before moving the tubular support in a proximal direction so as to draw the cover material inside-out from a distal-most position wherein the cover extends at least distally of the opening to a proximal-most position wherein the cover extends proximally of the opening.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

FIG. 4B shows a partial cross-sectional view of the sealing system of FIG. 4A.

FIGS. 5-7 show schematic views of the sealing system of FIG. 1 as the hollow tube is retracted away from the opening to a second position.

FIG. 11A shows a schematic view of the sealing system of FIG. 10 in a first position within a left ventricle.

FIG. 11B shows a schematic view of the sealing system of FIG. 10 in a second position outside of a left ventricle.

FIG. 11C shows a schematic view of the sealing system of FIG. 10 with the hollow tube and hub removed.

FIG. 13 shows a partial cross-sectional, schematic view of another embodiment of a sealing system having a hollow tube, a cover material, a ring and a hub, the hollow tube having a one or more protrusions.

FIG. 14C shows a schematic view of the sealing system of FIG. 14A with the C-clip anchor in a deployed position.

DETAILED DESCRIPTION

The present specification and drawings provide aspects and features of systems and methods for sealing openings in an anatomical wall in the context of several embodiments of devices, systems and methods. These embodiments may be discussed in connection with specific surgical procedures, such as a percutaneous and/or transpical surgical procedure. Accordingly, reference may be made to specific types of anatomical tissue such as cardiac tissue. However, it is to be understood that the features and concepts discussed herein, such as the controlled positioning features, deployment features, securing features, and sealing features, can be applied to procedures involving other organs and/or other anatomical walls. Moreover, while certain of the devices herein are described as being hollow and/or having a lumen, it should be understood that in some embodiments, the devices can be solid and/or not have a lumen. In addition, particular features of the devices, systems, and methods should not be taken as limiting, and features of any one embodiment discussed herein can be combined with features of other embodiments as desired and when appropriate.

As used to describe the devices, systems and methods of the present disclosure, "proximal" refers to a location of components that are closer to the operator, and "distal" refers to a location of the components that are further from the operator. Based on the orientation of the figures, "proximal" would refer to a location to the right of the figures whereas "distal" would refer to a location to the left of the figures.

Figure 1:
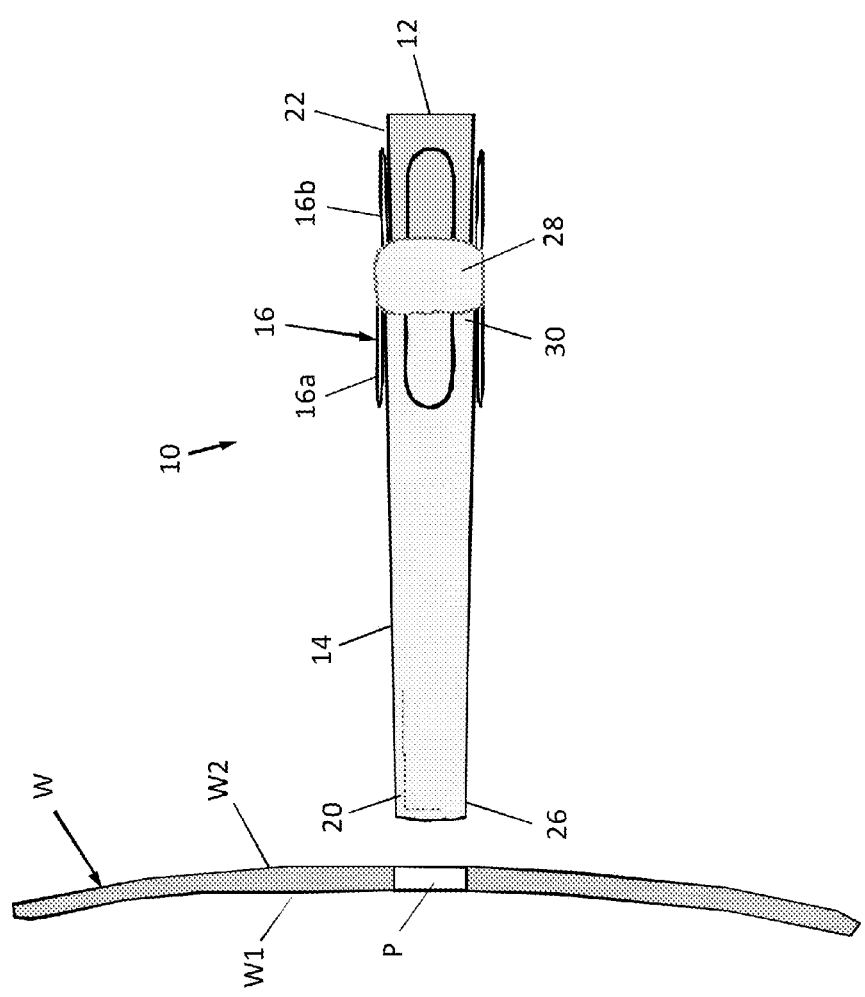
FIG. 1 shows a schematic view of an embodiment of a system for sealing an opening in an anatomical wall, the system having a hollow tube, a bio-compatible cover material, and anchors.

With reference first to the embodiment of FIG. 1 which illustrates puncture sealing system 10, the sealing system 10 can be designed to seal an opening and/or puncture P in an anatomical wall, such as an internal wall W or an external wall of a patient, where the wall W may include any organ or lumenal wall, including but not limited to, a cardiac wall such as an atrial wall or a ventricle wall. As shown in the illustrated embodiment, the sealing system 10 can include a tubular support or hollow tube 12 which can support a bio-compatible cover material or sealable material 14 and an anchor assembly which can include a plurality of anchors 16, the anchor assembly being designed to retain the cover material 14 over the opening and/or puncture P in the wall W. As shown in the illustrated embodiment, the cover material 14 can extend distally from the anchors 16 to cover at least a portion of the hollow tube 12. The anchors 16 can be fitted over the outer surface of the hollow tube 12 and, in some embodiments, can be positioned proximal a central portion of the hollow tube 12.

In some embodiments, the cover material 14 and/or the anchors 16 can snugly fit over the outer surface of the hollow tube 12 such that the anchors 16 are retained on the hollow tube 12 via a friction fit. This can be advantageous in reducing the likelihood that the anchors 16 are dislodged from the hollow tube 12 prior to positioning the anchors 16 at the target site. Other mechanisms can also be used to retain the anchors 16 on the hollow tube 12. For example, the anchors 16 can be attached to the hollow tube 12 via fasteners such as rivets, screws, bolts, sutures, clips or similar, via adhesives or similar, via welding the anchors 16 to the hollow tube 12 or vice versa, any other mechanism or technique as desired, or a combination of such mechanisms and/or techniques. In some embodiments, the cover material 14 and/or anchors 16 can be sufficiently spaced from the outer surface of the hollow tube 12 such that the cover material 14 and/or anchors 16 freely float over the hollow tube 12.

As shown in the embodiment of FIG. 1, the hollow tube 12 can have an elongate body with a distal end 20 and a proximal end 22. As shown in the illustrated embodiment, the hollow tube 12 may be generally cylindrical in shape and tapered. It should be understood that other shapes, including shapes having non-circular cross-sections such as ovals and/or polygons, are also contemplated and can also be used as desired. In some embodiments such as that shown in FIG. 1, the hollow tube 12 can have a lumen through which other devices, such as surgical devices and prostheses, can pass. In this manner, the sealing system 10 can advantageously remain placed within the opening and/or puncture P while steps of a surgical procedure are being performed. In some embodiments, the hollow tube 12 can be designed such that a portion of the hollow tube 12, such as a portion proximate the distal end 20, is tapered whereas the remainder of the hollow tube 12 is non-tapered. Tapering can beneficially facilitate insertion of the hollow tube 12 into an opening and/or puncture P in the anatomical wall W. Of course, it is also contemplated that the hollow tube 12 can have a non-tapered design. In some embodiments, the taper can range from about 0.1 degrees to about 30 degrees, from about 1 degree to about 15 degrees, from about 3 degrees to about 10 degrees, about 5 degrees, or any other angle as desired. In some embodiments, the taper can be less than about 15 degrees, less than about 10 degrees, less than about 5 degrees, or any other angle as desired.

The cover material 14 can be formed from one or more of a number of bio-compatible materials. In some embodiments, the cover material 14 can be formed from a bio-compatible material which provides the functional quality of sealing against the permeation of high pressure blood or other fluid. Such a material can be particularly advantageous in situations where the cover material 14 is subject to high pressures such as when the cover material 14 is used to seal an opening and/or puncture in a cardiac wall or tissue proximate a cardiac wall. As noted above, the cover material 14 can be formed from a combination of different materials. For example, it is contemplated that material of the cover material 14 used to attach the cover material 14 to the anchors 16 can be different the material in other portions of the cover material 14.

In some embodiments, the cover material 14 can be formed from a material having similar properties to that of the tissue which it is intended to replace and/or that of the surrounding tissue. In this manner, the cover material 14 can function similarly to that of the original tissue or surrounding tissue which reduces the likelihood of complications. For example, the cover material 14 can have a similar modulus of elasticity, resiliency, mass, permeability and/or any other characteristic to that of the tissue which it is intended to place and/or that of the surrounding tissue. In some embodiments, such as those where the cover material 14 is to seal an opening and/or puncture through a cardiac wall, the cover material 14 can be formed from materials such as bovine, equine or porcine pericardial tissue, a synthetic material and/or a textile-like material. In some embodiments, the cover material 14 can be formed from polymers such as polytetrafluoroethylene (PTFE), expanded polytetrafluoroethylene (ePTFE), polyesters, polyactide (PLA), poly-L-lactide (PLLA), poly-D-lactide (PDLA), polyethylene (PE), polyethylene terephthalate (PET), fluorinated ethylene propylene (FEP), variants of these polymers, and any other polymers and/or materials as desired. As noted above, these materials can be formed in a textile-like manner such as a weave. Any other bio-compatible material can be used. It should be understood that materials which have properties dissimilar to that of the tissue which the cover material 14 is intended to replace and/or that of the surrounding tissue are also contemplated for use in forming the cover material 14. Such materials can be used, for example, when such dissimilar properties can provide therapeutic benefits to the patient. For example, use of materials having dissimilar properties can be advantageous if the tissue which cover material 14 is intended to replace was diseased.

In some embodiments, the material can be designed to promote the formation of tissue around, onto and/or into the cover material 14. This can be advantageous in enhancing the seal between the cover material 14 and the tissue surrounding the opening and/or puncture. In some embodiments, the material can be designed to be permanent whereas in other embodiments the material can be designed to be bio-absorbable. A bio-absorbable material can be advantageous in situations where natural tissue is formed during the healing process and this natural tissue seals the wound such that the cover material 14 is no longer needed.

In such an embodiment, the anchors 16 or any other component left within the body can also be designed to be bio-absorbable.

With continued reference to the embodiment of FIG. 1, a distal portion 26 of cover material 14 can be designed to fit snugly over the distal end 20 of the hollow tube 12. As shown in the illustrated embodiment, the end of the cover material 14 can be inverted and extended into the lumen of the hollow tube 12 and attached to an internal surface proximate the distal end 20 of the hollow tube 12. In some embodiments, the end of the cover material 14 be attached to an external surface proximate the distal end 20 of the hollow tube 12. Of course, it should be understood that the cover material 14 can be attached at any other position along the internal and/or external surfaces of the hollow tube 12 including, but not limited to, a central portion of the hollow tube 12 between the distal and proximal ends 20, 22. For example, in some embodiments, the end of the cover material 14 can extend further proximally within the lumen of the hollow tube 12 and be attached to an internal surface proximate the proximal end 22 of the hollow tube 12. In this manner, a cover material 14 having an extended length can be used. The cover material 14 can be attached to the hollow tube 12 via fasteners such as rivets, screws, bolts, sutures, clips, or similar, via adhesives or similar, via welding the cover material 14 to the hollow tube 12 or vice versa, any other mechanism or technique as desired, or a combination of such mechanisms and/or techniques.

The cover material 14 can include a bundled portion 28 of such material at a proximal end 30 of the cover material 14 to cover at least a portion of the anchors 16. As shown in the illustrated embodiment, the bundled portion 28 can be a portion of the cover material 14 that is sutured or attached to the anchors 16. In some embodiments, the bundled portion 28 can have an equivalent thickness and/or dimensions to that of the other portions of the cover material 14. The bundled portion 28 can function as an internal and/or external liner of the anchors 16. It is also contemplated that the bundled portion 28 can be formed such that the bundled portion 28 has a greater thickness than the remaining portion of the cover material 14. In some embodiments, the bundled portion 28 can be formed by folding the cover material 14 into one or more layers at the proximal end 30 of the cover material 14. The multiple layers of the bundled portion 28 can then be secured together via use of sutures, staples and/or other types of fasteners, adhesives, welded and/or any other mechanism for attaching the multiple layers together as desired. In some embodiments, the bundled portion 28 can have a unitary structure rather than a layered structure. For example, during the manufacturing process, the bundled portion 28 can be formed to have a greater thickness than the remaining portions of the cover material 14. As will be described below in further detail, the bundled portion 28 can be secured to the anchors 16 and/or any structure between the anchors 16.

Figure 2:
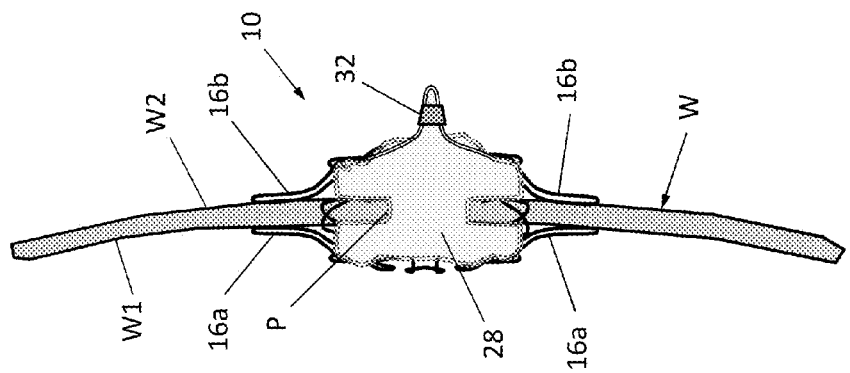
FIG. 2 shows a schematic view of the sealing system of FIG. 1 with the anchors deployed within an opening in a heart wall.

With continued reference to the embodiment of FIG. 1, the anchors 16 can include a plurality of distal anchors 16a and a plurality of proximal anchors 16b. The distal and/or proximal anchors 16a, 16b can be made of flexible material, preferably a shape-memory material such as nitinol or other shape-memory metal or polymer, that permits a first, delivery position (as shown in FIG. 1) and a second, deployed position or wall engagement position (as shown in FIG. 2). As shown in the illustrated embodiment, in the first, delivery position, the distal and proximal anchors 16a, 16b are movable towards the hollow tube 12 and can rest radially astride the distal ends 26, 20 of cover material 14 and hollow tube 12, respectively, for delivery to and positioning at a target site. In the second, deployed position, the distal and proximal anchors 16a, 16b are movable outwardly to engage the surrounding tissue at the target site when deployed. As shown in the illustrated embodiment, the distal and proximal anchors 16a, 16b can rotate to engage the surrounding tissue at the target site.

In some embodiments, the anchors 16 can have a single unitary configuration. The anchors 16 can include a frame portion (not shown) between the distal and proximal anchors 16a, 16b which connect the distal anchors 16a to the proximal anchors 16b. In some embodiments, the distal and proximal anchors 16a, 16b can be connected via the bundled portion 28. In some embodiments, the anchors 16 can be formed from a plurality of discrete anchors secured together. For example, in some embodiments, one or more distal anchors 16a and one or more proximal anchors 16b can form a discrete unit which can then be secured together to form the anchors 16. In some embodiments, one or more distal anchors 16a form a discrete unit and one or more proximal anchors 16b form a discrete unit which can then be secured together to form the anchors 16. As shown in the sealing system 10 of FIG. 1, the proximal end 30 of cover material 14 can be positioned at or proximate the junction of the distal and proximal anchors 16a, 16b so that the anchors 16 and cover material 14 function together to securely engage and seal the tissue W surrounding the opening and/or puncture P in the tissue to result in a sealed closure of the puncture, as shown in FIG. 2 and as described further below.

As shown in the embodiment of FIG. 2, the distal anchors 16a have moved to their respective second, deployed position to securely engage the distal side W1 of the tissue wall W while the proximal anchors 16b have moved to their respective second, deployed position to securely engage the proximal side W2 of the tissue wall W. It should be appreciated that the distal side W1 can be an internal surface of the tissue wall W while the proximal side W2 can be an external surface of the tissue wall W. As will be explained in further detail below with reference to FIGS. 3-8, the proximal portion 26 of cover material 14 has been withdrawn inwardly from the distal side W1 of the wall to the proximal side W2 of the wall and cut and closed with a fitting 32 to finish deployment. Moreover, as shown in the embodiment of FIGS. 1 and 2, the bundled portion 28 of the cover material 14 can be attached to the distal and/or proximal anchors 16a, 16b. In some embodiments, the bundled portion 28 can be positioned radially outward from an outwardly facing side of the anchors 16 when the distal and proximal anchors 16a, 16b are in the first, delivery position as shown in FIG. 1 such that, when the anchors 16a, 16b are in the second, deployed position as shown in FIG. 2, the bundled portion 28 is placed direct contact with the wall W between the distal and proximal anchors 16a, 16b. The bundled portion 28 can be designed such that it contacts at least a portion of the distal side W1, the proximal side W2, and/or the rim between the two sides W1, W2 of the wall W during the process of securing the anchors 16 to the wall W and/or after securing the anchors 16 to the wall W. This can advantageously enhance the sealing effect and reduce the likelihood that fluid will flow past the anchors 16 and/or cover material 14. It should also be noted that because the bundled portion 28 may simply take the form of an outer or inner lining relative to the anchors 16, after the cover material 14 has been withdrawn inwardly from the distal side W1 of the wall to the proximal side W2 of the wall, there may be an opening (not shown) through the bundled portion 28 at the distal end of the anchors 16 that would be closed by the fitting 32.

In some embodiments, the bundled portion 28 can be attached to an inwardly facing side of the anchors 16 to form a liner along the interior of the anchors 16. This can advantageously enhance the sealing effect of the anchors 16 and cover material 14. In some embodiments, the bundled portion 28 can be attached to both an outwardly facing side and an inwardly facing side of the anchors 16. The bundled portion 28 can be attached to the anchors 16 via fasteners such as rivets, screws, bolts, sutures, clips or similar, via adhesives or similar, via welding the cover material 14 to the anchors 16 or vice versa, any other mechanism or technique as desired, or a combination of such mechanisms and/or techniques.

Figure 3:
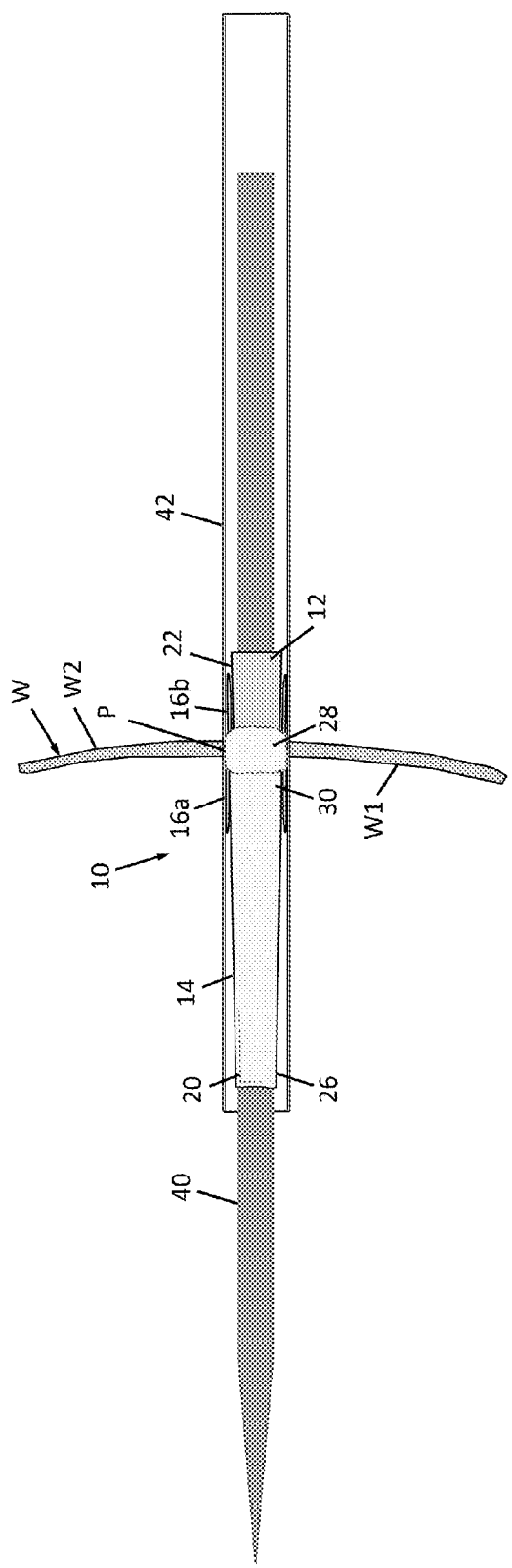
FIG. 3 shows a schematic view of the sealing system of FIG. 1 within a delivery catheter and having an introducer catheter passing therethrough, the anchors being in a delivery position.

With reference now to the embodiment of FIGS. 3 through 8, steps in the deployment of the sealing system 10 of FIG. 1 are now described. With reference first to the embodiment of FIG. 3, in some embodiments the sealing system 10 may be delivered percutaneously to the puncture site P via an introducer catheter 40 or the like and can be sheathed within a delivery catheter 42. In some embodiments, the introducer catheter 40 can serve as a dilator which can form and/or expand the opening and/or puncture P within the anatomical wall W. The delivery catheter 42 can compress the distal and proximal anchors 16a, 16b against the cover material 14 and the hollow tube 12 and retain the anchors 16 in the first, delivery position. As shown in the embodiment of FIG. 3, the anchors 16 can be positioned at a target location proximate the opening and/or puncture P within the delivery catheter 42 with a distal end 20 of the hollow tube 12 positioned distal relative to the anchors 16 and the opening and/or puncture P and the proximal end 22 of the hollow tube 12 positioned proximal relative to the anchors 16 and the opening and/or puncture P. During this step, the introducer catheter 40 can be removed and other devices, such as surgical devices and/or prostheses, can be inserted past the wall W via the delivery catheter 42 and through the hollow tube 12 to perform other steps of a surgical procedure. In some embodiments, the delivery catheter 42 can be removed prior to performance of other steps of a surgical procedure such that surgical device and/or prostheses are passed through the hollow tube 12 and not the delivery catheter 42. For example, in a surgical procedure involving a heart valve replacement, a heart valve can be transported through the delivery catheter 42 and past the sealing system 10. It should be appreciated that the sealing system 10 described herein can therefore advantageously allow the surgical procedure to be performed in an effective and efficient manner through the same opening and/or puncture P. Moreover, it should be appreciated that the embodiment described herein need not be delivered percutaneously and can be used in open or semi-open surgical procedures such as a transapical surgical approach.

Figure 4A:
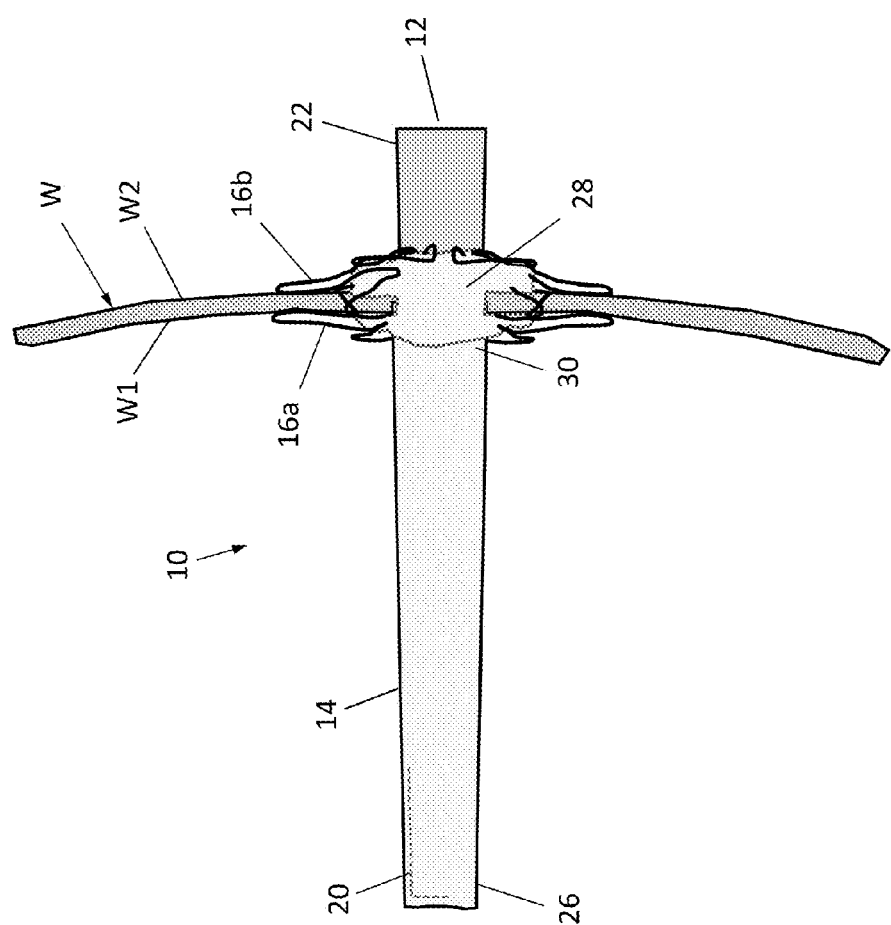
FIG. 4A shows a schematic view of the sealing system of FIG. 1, wherein the hollow tube is positioned within an opening in a heart wall in a first position with the anchors being in a deployed position.

With reference now to the embodiment of FIGS. 4A and 4B, the delivery catheter 42 can be removed, leaving the sealing system 10 appropriately placed in-situ within the opening and/or puncture P of wall W, the distal and proximal anchors 16a, 16b can flare outwardly to snugly grasp the distal and proximal sides of the wall W1, W2 respectively. In some embodiments where the distal and/or proximal anchors 16a, 16b are formed of a shape-memory material biased towards the second, deployed position, this can automatically occur as the anchors 16a, 16b are uncovered from the delivery catheter 42. In some embodiments, steps of a surgical procedure can also be performed through the hollow tube 12 during this stage. For example, in one embodiment the hollow tube 12 may extend into the left ventricle of the heart while the distal and proximal anchors 16a, 16b engage the wall of the heart at a transapical opening. A replacement heart valve, such as a mitral valve replacement, may be delivered through the hollow tube 12 and deployed at the native mitral valve.

Figure 6:
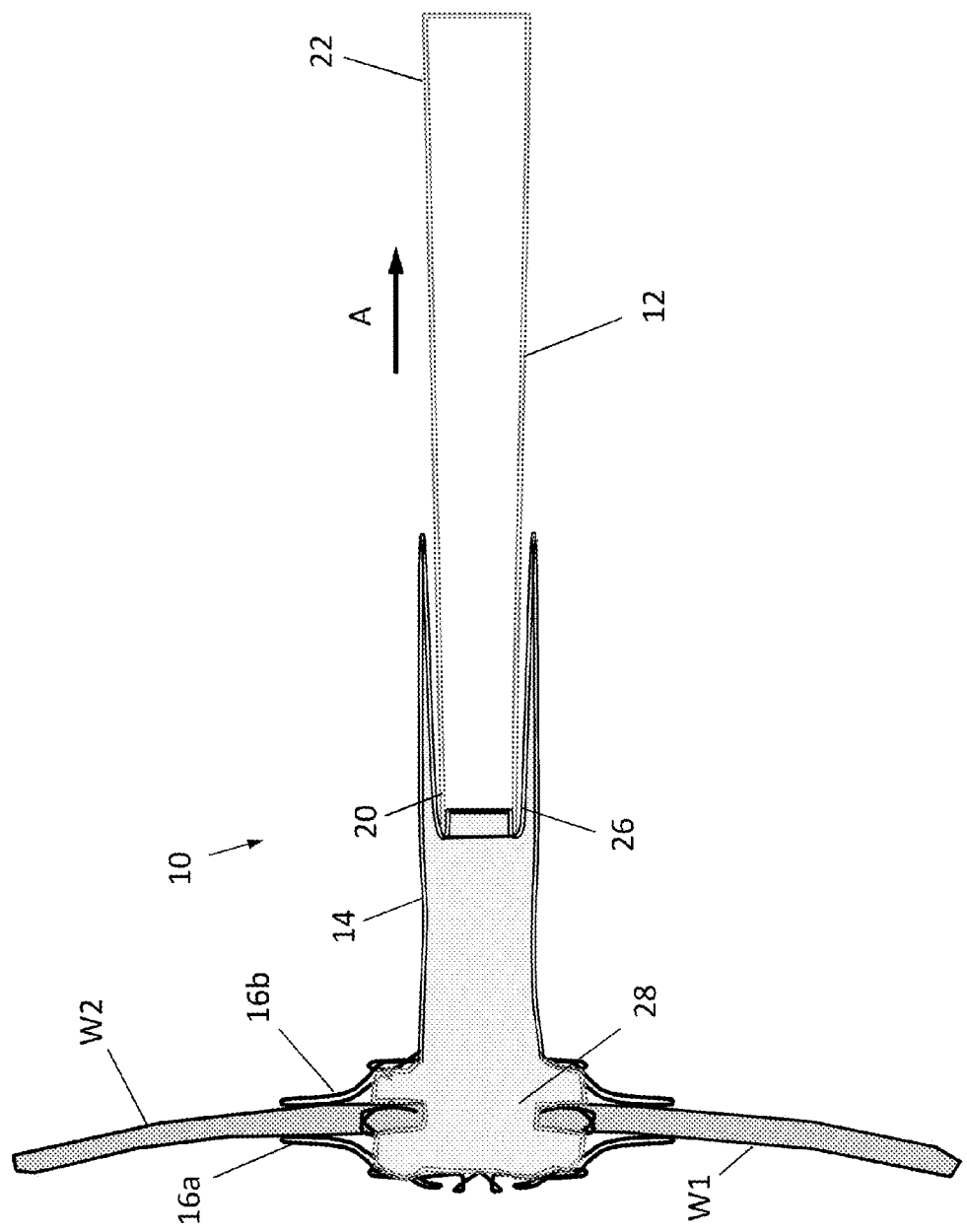
Figure 7:
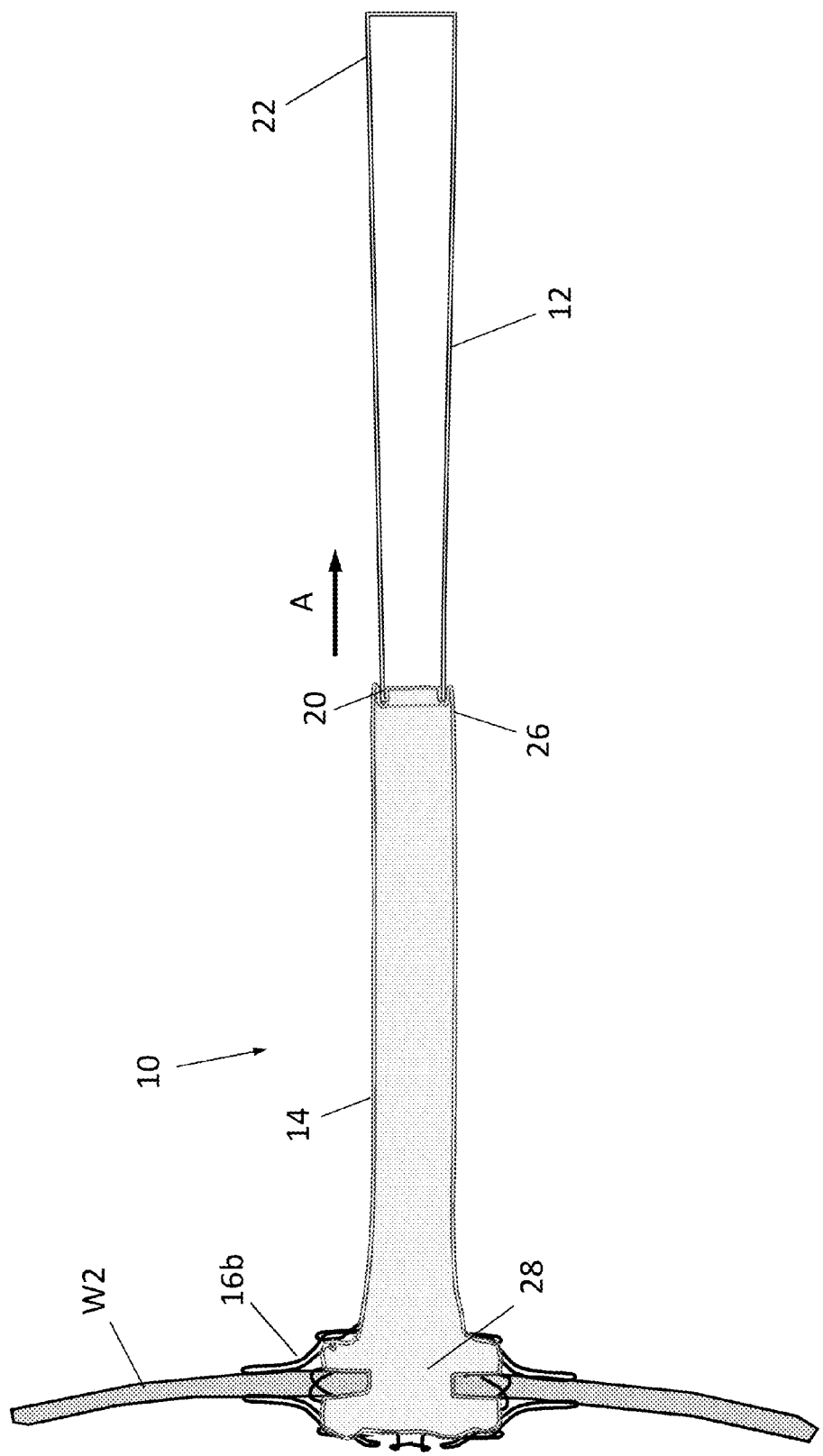

With reference now to the embodiment of FIGS. 5-7, after a desired procedure has been completed, the hollow tube 12 may be directed or retracted proximally in the direction of arrow A. As shown in the embodiments of FIGS. 5-7, retraction proximally of the hollow tube 12 can result in simultaneously pulling the cover material 14 inside-out (i.e., the surface of the cover material 14 originally facing inwardly towards the hollow tube 12 is now facing outwardly away from the hollow tube 12). Continued pulling of the proximal end 22 of tube 12 in the direction of arrow A results in the position shown in FIG. 7, where the distal end 20 of the tube 12 and what was once the distal end of the cover material 14 are now positioned proximal relative to the anchors 16a, 16b and bundled portion 28 of material.

Figure 8:
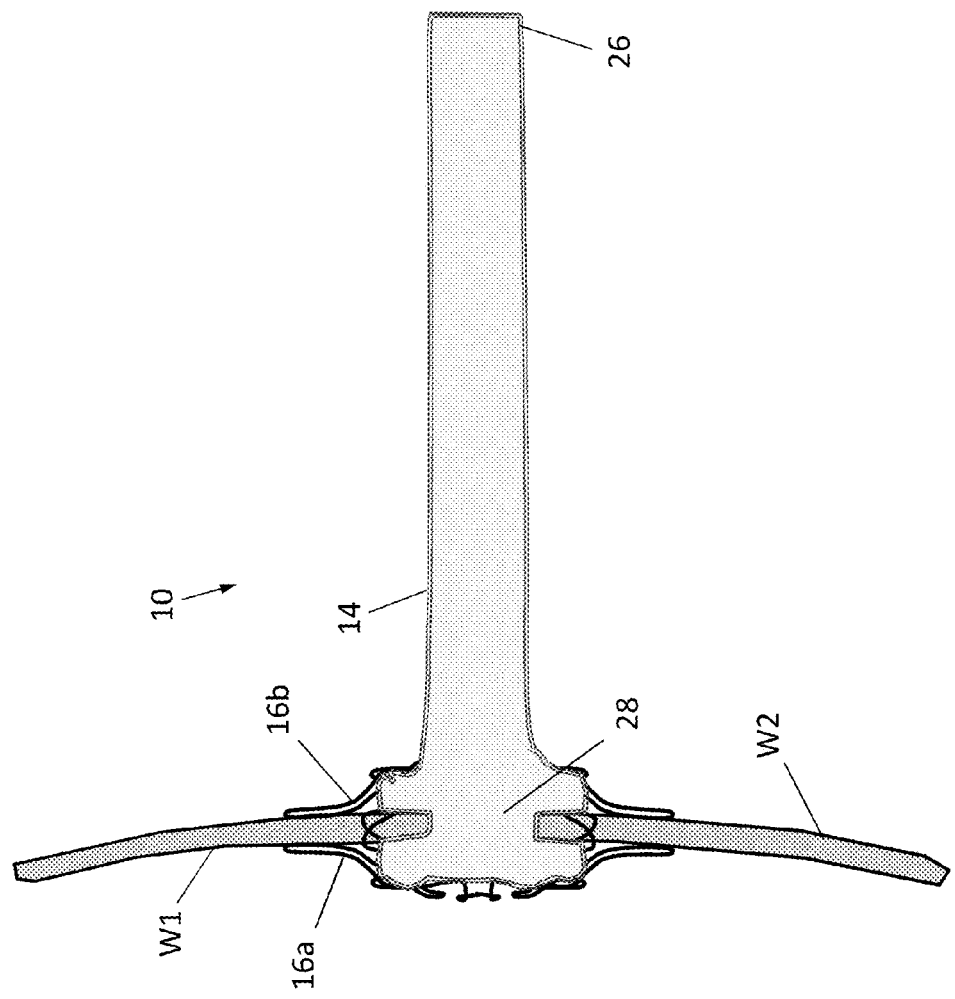
FIG. 8 shows a schematic view of the sealing system of FIG. 1 with the hollow tube detached from the cover material.

With reference now to the embodiment of FIG. 8, once the tube 12 has reached a sufficiently proximal position relative to the anchors 16, a substantial portion, if not substantially the entirety, of the cover material 14 is now inside-out, at which point the tube 12 may be removed completely, leaving behind the anchors 16 and the cover material 14. As alluded to above, the cover material 14 can be severed proximal the anchors 16 and tied off using a fitting or clip 32 or other means of sealing the end of the material, as shown in FIG. 2. For example, the cover material 14 can be tied off using staples, sutures or other fasteners, adhesives or similar, welding or similar techniques, any other device or technique as desired, or a combination of such mechanisms and/or techniques. In some embodiments, the cover material 14 can be severed by cutting the cover material 14. In some embodiments, the attachment between the cover material 14 and the hollow tube 12 can be severed by pulling the hollow tube 12 proximal relative to the cover material 14.

Figure 9:
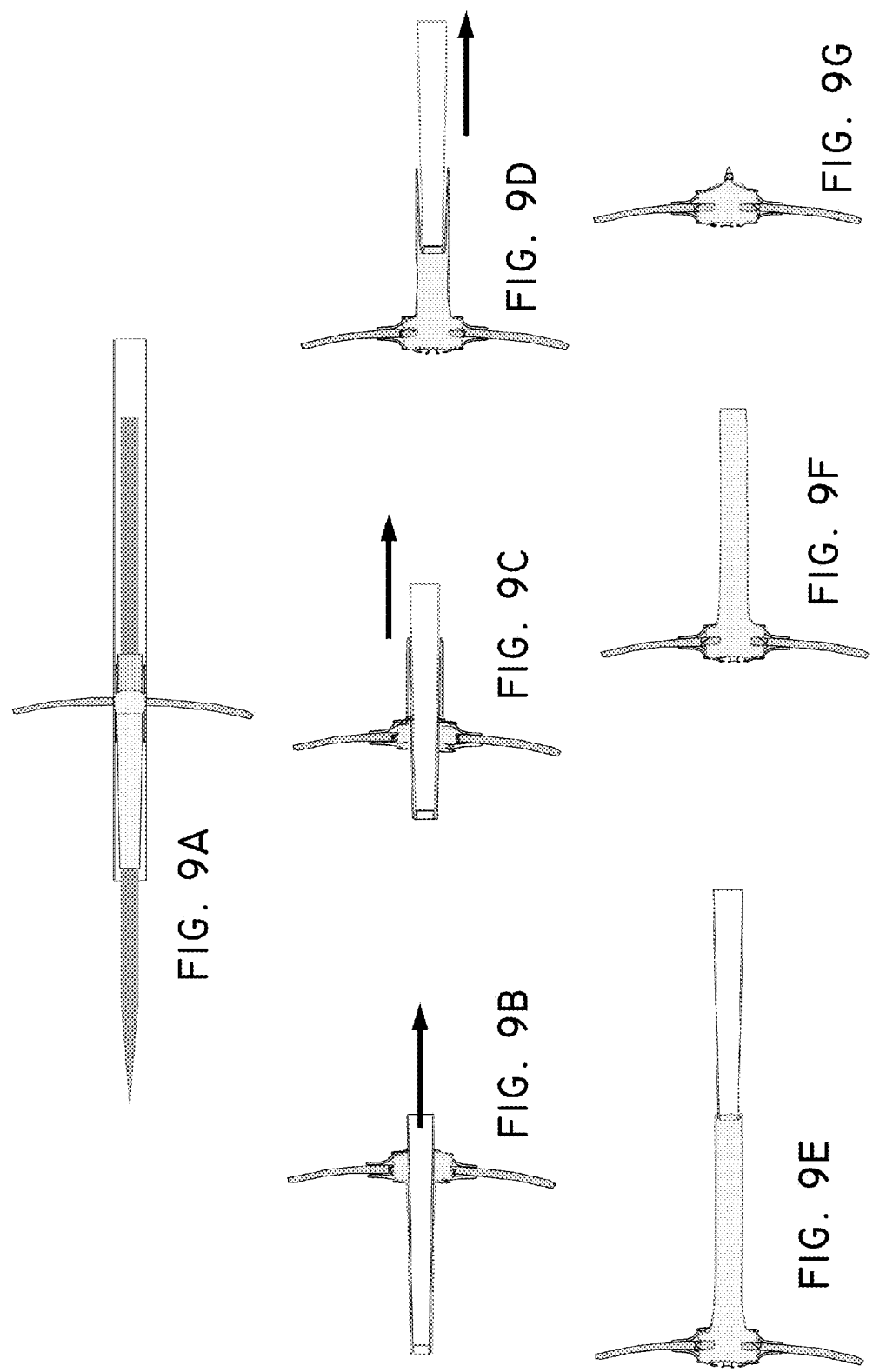
FIGS. 9A-9G show schematic views of FIGS. 3 through 8 and FIG. 2 in smaller format, illustrating one preferred sequence of deployment.

FIGS. 9A-9G are schematic views illustrating one preferred sequence of utilizing the devices described in FIGS. 1-8 above, with FIG. 9A corresponding to FIG. 3, FIG. 9B corresponding to FIGS. 4A and 4B, FIG. 9C corresponding to FIG. 5, FIG. 9D corresponding to FIG. 6, FIG. 9E corresponding to FIG. 7, FIG. 9F corresponding to FIG. 8, and FIG. 9G corresponding to FIG. 2.

With reference now to the embodiment of FIG. 10 which illustrates a sealing system 110, the sealing system 110 can be designed to seal an opening and/or puncture in an anatomical wall of a patient similar to that described in connection with the embodiment of FIGS. 1-9G. The sealing system 110 can include components, such as tubular support or hollow tube 112 and/or cover material or sealable material 114, having features and/or functionality similar to those described in connection with sealing system 10 such as hollow tube 12 and cover material 14. Accordingly, it should be understood that features and/or functionality of components of sealing system 10 can also apply to components of sealing system 110.

With continued reference to the embodiment of FIGS. 10 and 11A-11C which illustrates the sealing system 110, the hollow tube 112 can support a bio-compatible cover material or sealable material 114 and an anchor assembly which can include a donut, ring or button 116, the anchor assembly being designed to retain the cover material 114 over the opening and/or puncture in the wall W (as shown in FIGS. 11A-11C). As shown in the illustrated embodiment, the cover material 114 can extend distally from the ring 116 to cover at least a portion of the hollow tube 112. As mentioned above, the hollow tube 112 can have features and functionality similar to that of hollow tube 12 such as, but not limited to, a lumen through which surgical devices can pass and/or a tapered portion (not shown).

As shown in the illustrated embodiment, the system 110 can include a hub 118. The hub 118 can include features which facilitate manipulation of the hub 118 by an operator who is grasping the hub 118 by hand. Such features can include varying diameters along its length as shown in the illustrated embodiment, nubs or protrusions along the surface which can enhance grip of the hub 118, and any other such features as desired. Moreover, as shown in the illustrated embodiment, the hub 118 can have a greater diameter compared to the hollow tube 112. This can allow an operator to grasp a distal face 120 of the hub 118 when pulling or retracting the hub 118 proximally. The hub 118 can include a lumen through which devices can pass. The lumen can be positioned such that it is concentric with a lumen of the hollow tube 112 and/or have a cross-sectional dimension which matches that of a lumen of the hollow tube 112. In some embodiments, a proximal end 122 of the hollow tube 112, or a portion proximate the proximal end 122, can be attached directly to the hub 118 via any fasteners such as rivets, screws, bolts, sutures, clips or similar, via adhesives or similar, via welding the hollow tube 112 to the hub 118 or vice versa, any other mechanism or technique as desired, or a combination of such mechanisms and/or techniques. In some embodiments, the hollow tube 112 and the hub 118 can form an integral or monolithic unit.

In some embodiments, the hollow tube 112 and the hub 118 can have a suspension and/or dampening element (not shown) placed between the tube 112 and the hub 118. The suspension and/or dampening elements can be placed between a proximal end 120 of the tube 112 and a distal end 122 of the hub 118. The hollow tube 112 and the hub 118 can be attached together via the suspension and/or dampening element. The suspension and/or dampening element can be in the form of a spring including, but not limited to, a coil spring, a wave spring such as a flat wire wave spring, a single turn wave spring or other types of wave springs, and any other types of springs. The suspension and/or dampening element can be in the form of a washer having spring-like properties such as a Belleville washer, a curved disc washer, a wave washer, a split washer, or other types of washers. In some embodiments, the suspension and/or dampening element can be in the form of any other type material having suspension and/or dampening properties such as a spacer made from a soft, resilient material. As should be appreciated, use of a suspension and/or dampening element between the hollow tube 112 and the hub 118 can facilitate placement of the ring 116 adjacent tissue W as it can absorb minor movements in the hub 118 such as those which may be a result of the operator's movements.

As shown in the illustrated embodiment, the ring 116 can be sized and shaped such that it floats over the outer surface of the hollow tube 112. In some embodiments, the cover material 114 and/or the ring 116 can snugly fit over the outer surface of the hollow tube 112 such that the ring 116 is retained on the hollow tube 112 via a friction fit. As shown in the illustrated embodiment, the ring 116 can be in the form of a ring having an inner diameter and an outer diameter. Other types of shapes, including non-circular and polygonal shapes, can be used for the ring 116 as desired. For example, a non-circular shape can be used if the opening in the wall W is non-circular or if a non-circular shape can be advantageous based on the application.

Similar to cover material 14 of sealing system 10, the cover material 114 can be formed from one or more of a number of bio-compatible materials and/or a combination of different materials. The properties of the bio-compatible materials can be chosen, for example, based on the application for the sealing system 110. For purposes of brevity, reference should be made to the discussion of materials and material properties for cover material 14 as said discussion also applies to cover material 114.

Figure 10:
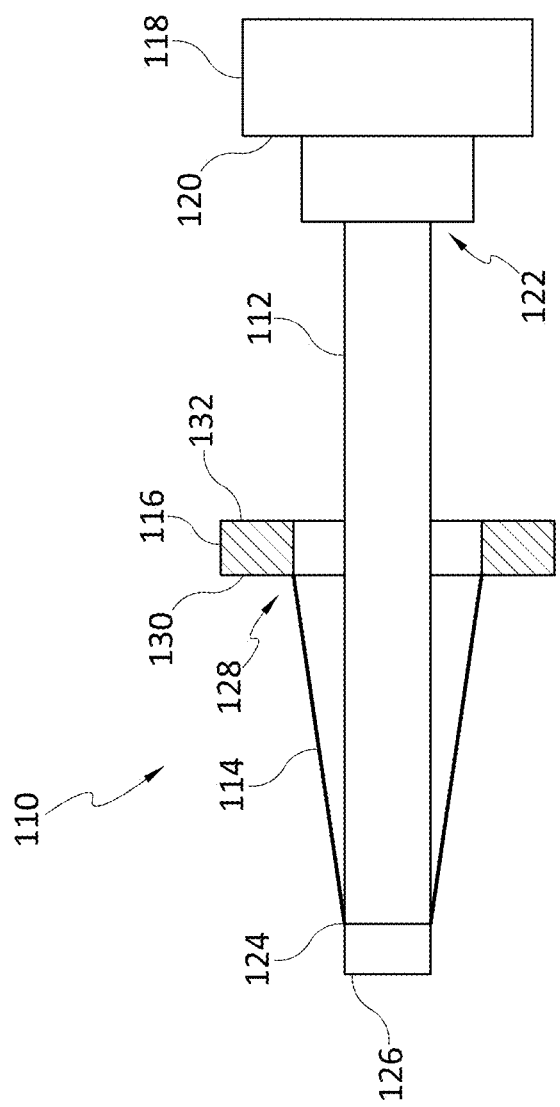
FIG. 10 shows a partial cross-sectional, schematic view of an embodiment of a sealing system having a hollow tube, a cover material, a ring and a hub.

With continued reference to the embodiment of FIG. 10 which illustrates the sealing system 110, a distal end 124 of cover material 114 can be attached to a portion proximate a distal end 126 of the hollow tube 112. Of course, similar to cover material 14 of sealing system 10, the end of the cover material 114 can be inverted and extended into a lumen of the hollow tube 112 and attached to an internal surface at any position including a portion proximate the distal end 126 of the hollow tube 112, a portion proximate the proximal end 122 of the hollow tube 112, and/or a central portion between the distal and proximal ends 126, 122 of the hollow tube 112. Moreover, while the end 124 of the cover material 114 is illustrated as being attached to an external surface of portion of the hollow tube 112 proximate the distal end 126, it should be understood that the cover material 114 can be attached at any other position along the external surface of the hollow tube 112 including, but not limited to, a central portion of the hollow tube 112 between the distal and proximal ends 126, 122. As with cover material 14 of sealing system 10, the cover material 114 can be attached to the hollow tube 112 via fasteners such as rivets, screws, bolts, sutures, clips or similar, via adhesives or similar, via welding the cover material 114 to the hollow tube 112 or vice versa, any other mechanism or technique as desired, or a combination of such mechanisms and/or techniques.

As shown in the illustrated embodiment, the cover material 114 can be attached to the ring 116 at a proximal portion 128 of the cover material 114. In some embodiments, the proximal portion 128 of the cover material 114 can cover at least a portion, if not the entirety of, the distal face 130 of the ring 116. In this manner, the cover material 114 can advantageously be placed against the wall W to which the ring 116 is attached. This can beneficially further enhance the seal formed over the opening and/or puncture and reduce the likelihood that fluids flow around the cover material 114 and past the ring 116. In some embodiments, the cover material 114 can be attached to the distal face 130 via fasteners such as rivets, screws, bolts, sutures, clips or similar, via adhesives or similar, via welding the cover material 114 to the ring 116 or vice versa, any other mechanism or technique as desired, or a combination of such mechanisms and/or techniques. In some embodiments, the cover material 114 and the ring 116 can form an integral or monolithic unit.

Likewise, the cover material 114 can cover at least a portion, if not the entirety of, the proximal face 132 of the ring 116. In some embodiments, the cover material 114 can be attached to the proximal face 132 via the mechanisms and/or techniques discussed above in connection with the distal face 130. In some embodiments, the cover material 114 can cover the entire outer surface of the ring 116 and/or be attached to other surfaces of the ring 116.

In some embodiments, the ring 116 can include two or more separate components. For example, the ring 116 can be formed from two ring-shaped components. In some embodiments, the ring 116 can include one or more flanges placed between two or more of the components. These flanges can be a portion of the cover material 114 which is attached between two or more of the ring-shaped components. The flanges can be separate from the cover material 114. In some embodiments, the flange can facilitate attachment of the cover material 114 to the ring-shaped components. The two or more separate components can be formed from different materials. The ring-shaped components can be formed from one or more materials, such as polytetrafluoroethylene (PTFE), and the flange can be formed from one or more materials, such as expanded polytetrafluoroethylene (ePTFE). The separate components can then be coupled together via fasteners such as rivets, screws, bolts, sutures, clips or similar, via adhesives or similar, via welding the two or more components together, any other mechanism or technique as desired, or a combination of such mechanisms and/or techniques.

The ring 116 can be formed from one or more of a number of bio-compatible materials. The bio-compatible materials and properties of such materials described in connection cover materials 14, 114 can also be used for forming the ring 116. In some embodiments, the ring 116 can be formed from a bio-compatible material which can withstand high pressure fluids. Such a material can be particularly advantageous in situations where the ring 116 is used to seal an opening and/or puncture of an anatomical wall subject to such high pressures. For example, such a material can be advantageous when the ring 116 is used to seal an opening and/or puncture in a cardiac wall or tissue proximate the cardiac wall. In some embodiments, the ring 116 can be formed from a material which facilitates the placement of fasteners, such as staples or sutures, through the ring 116 for attaching the ring 116 to tissue. Accordingly, the ring 116 can be formed from a textile-like or felt-like material which can advantageously allow sutures to pass from the proximal face 132 to the distal face 130 and vice versa. The ring 116 can be formed from a natural or synthetic material. In some embodiments, the ring 116 can be formed from polymers such as polytetrafluoroethylene (PTFE), expanded polytetrafluoroethylene (ePTFE), polyesters, polyactide (PLA), poly-L-lactide (PLLA), poly-D-lactide (PDLA), polyethylene (PE), polyethylene terephthalate (PET), fluorinated ethylene propylene (FEP), variants of these polymers, and any other polymers and/or materials as desired. As noted above, these materials can be formed in a textile-like manner such as a weave. Any other bio-compatible material can be used. In some embodiments, the material can be designed to promote the formation of tissue around, onto and/or into the ring 116 which can further enhance the attachment of the ring 116 to the tissue. In some embodiments, the material can be designed to be permanent whereas in other embodiments the material can be designed to be bio-absorbable. A bio-absorbable material can be advantageous in situations where natural tissue is formed during the healing process and this natural tissue seals the wound such that the ring 116 is no longer needed.

With reference now to the embodiment of FIGS. 11A-11C, steps in the deployment of the sealing system 110 are now described. The sealing system 110 can be delivered percutaneously to the target site or can be used during an open or semi-open surgical procedure such as a transapical surgical approach. With reference first to the embodiment of FIG. 11A, the hollow tube 112 can be inserted into an opening and/or puncture (not shown) in an anatomical wall W of a patient such as a ventricular wall of the left ventricle LV. The hollow tube 112 can be moved in a distal direction as shown by arrow B towards the wall W through the opening and/or puncture until the ring 116 is positioned adjacent or proximate the wall W. The opening and/or puncture can be one which was previously formed or one which was formed as the hollow tube 112 is being advanced towards the target site. For example, similar to that discussed in connection with the embodiment of FIG. 3, an opening and/or puncture can be formed and/or expanded via use of an introducer catheter or dilator through the lumen of the hollow tube 112. In some embodiments, the opening and/or puncture can be formed and/or expanded via the hollow tube 112 itself. As shown in the illustrated embodiment, the ring 116 can be positioned along a proximal side of the wall W, such as an external surface of the wall W, adjacent or proximate the opening and/or puncture. It is also contemplated that the ring 116 can be introduced through and into the puncture and placed along a distal side of the wall W, such as an internal surface of the wall W, adjacent or proximate the opening and/or puncture.

With continued reference to the embodiment of FIG. 11A, the ring 116 can be attached to the wall W of the patient. In some embodiments, the ring 116 can be attached to the wall W via sutures, staples, adhesives or other mechanisms and techniques typically used to couple anatomical tissue. Of course, the ring 116 can also be attached to the wall W via other mechanisms and/or techniques including, but not limited to, fasteners such as rivets, screws, bolts, sutures, clips, or similar, via adhesives, any other mechanism or technique as desired, or a combination of such mechanisms and/or technique. Preferably, the ring 116 is fastened to the wall W such that sufficient pressure is applied such that little to no leakage occurs around the ring 116. In embodiments where the cover material 114 covers at least a portion of the distal and/or proximal faces 130, 132 of the ring 116, the sutures, staples, adhesives or other mechanisms can also pass through the portions of the cover material 114 which cover the distal and/or proximal faces 130, 132 to further enhance the sealing effect.

It should be understood that, during the step described in connection with the embodiment of FIG. 11A, other devices can be inserted past the wall W via the hollow tube 112 to perform other steps of a surgical procedure. For example, in a surgical procedure involving a heart valve replacement, the heart valve can be transported through the hollow tube 112 and past the ring 116. It should be appreciated that the sealing system 110 described herein can advantageously allow the surgical procedure to be performed in an effective and efficient manner through the same opening and/or puncture.

With reference next to the embodiment of FIG. 11B, the hollow tube 112 can be directed or retracted proximally in the direction of arrow C. As shown in the embodiment of FIG. 11B, retraction proximally of the hollow tube 112 can result in simultaneously pulling the cover material 114 inside-out. As described above, the operator can retract the hollow tube 112 proximally via grasping the hollow tube 112 or the hub 118. Continued pulling or retraction of the proximal end 122 of tube 12 in the direction of arrow C can then result in the position shown in the embodiment of FIG. 11B, where the distal end 126 of the tube 112 and what was previously the distal end 124 of the cover material 114 are now positioned proximal relative to the ring 116.

With reference now to the embodiment of FIG. 11C, once the hollow tube 112 has reached a sufficiently proximal position relative to the ring 116, the hollow tube 112 may be removed completely, leaving behind the ring 116 and the cover material 114. As shown in the embodiment of FIG. 11C, the cover material 114 can be severed proximal the ring 116 and tied off using sutures. In some embodiments, a fitting or clip, similar to clip 32 as described in connection with the embodiment of FIG. 2, or other means of sealing the end of the cover material 114 can also be used in the alternative or in conjunction with the sutures. In some embodiments, the cover material 114 can be tied off using staples or other fasteners, adhesives or similar, welding or similar techniques, any other device or technique as desired, or a combination of such mechanisms and/or techniques. In some embodiments, the cover material 114 can be severed by cutting the cover material 114. In some embodiments, the attachment between the cover material 114 and the hollow tube 112 can be severed by pulling the hollow tube 112 proximal relative to the cover material 114.

With reference now to the embodiment of FIG. 12 which illustrates a sealing system 210, the sealing system 210 can be designed to seal an opening and/or puncture in an anatomical wall of a patient similar to that described in connection with the embodiments of FIGS. 1-11C. The sealing system 210 can include components, such as tubular support or hollow tube 212, cover material or sealable material 214, button, ring or donut 216 and/or hub 218, having features and/or functionality similar to those described in connection with sealing systems 10, 110 such as hollow tubes 12, 112, cover materials 14, 114, ring 116 and/or hub 118. Accordingly, it should be understood that features and/or functionality of components of sealing systems 10, 110 can also apply to components of sealing system 210.

Figure 12:
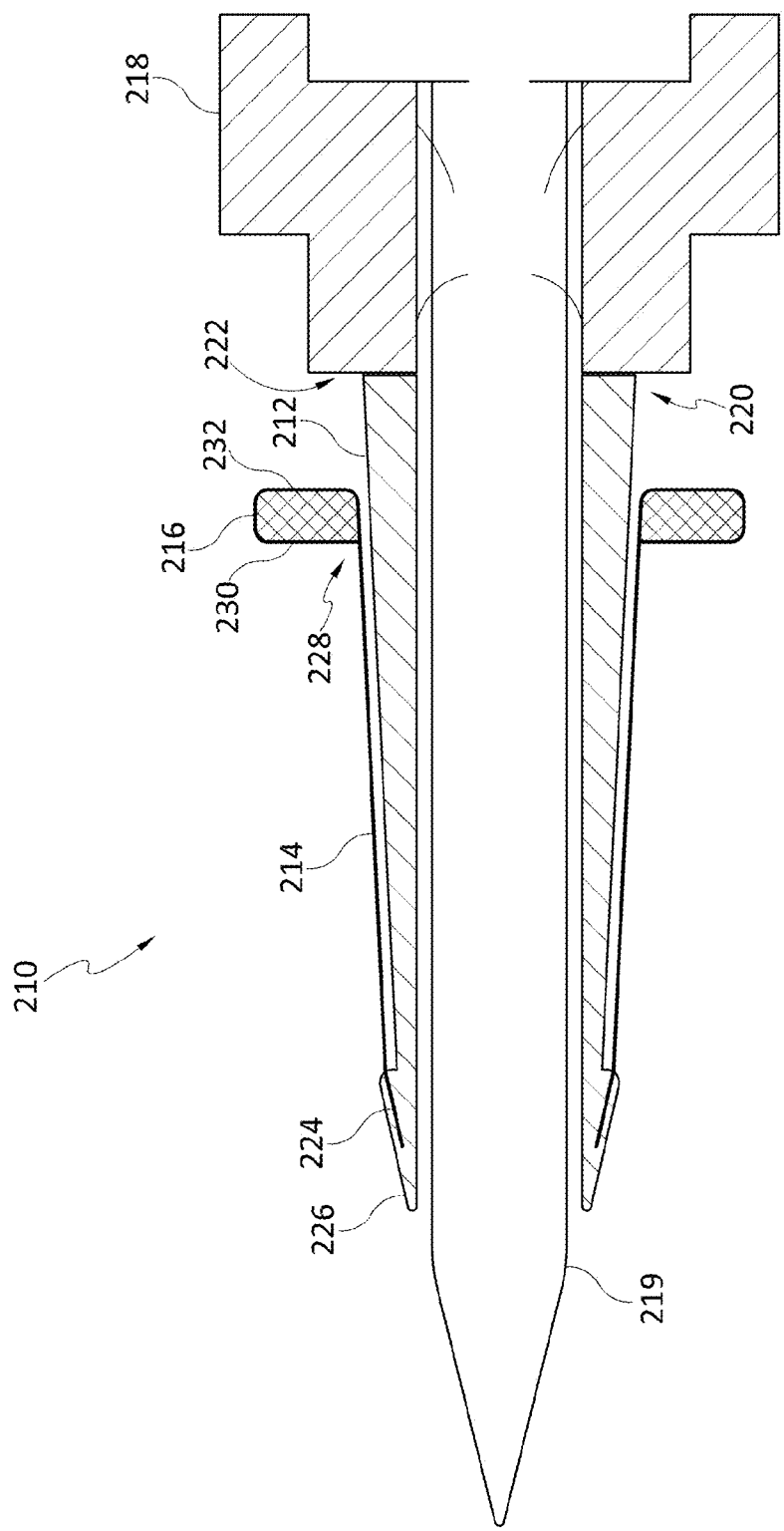
FIG. 12 shows a partial cross-sectional, schematic view of another embodiment of a sealing system having a hollow tube, a cover material, a ring and a hub, the hollow tube having a taper.

With continued reference to the embodiment of FIG. 12 which illustrates the sealing system 210, the hollow tube 212 can support a bio-compatible cover material or sealable material 214 and an anchor assembly which can include a donut, ring or button 216, the anchor assembly being designed to retain the cover material 214 over the opening and/or puncture in the wall. As shown in the illustrated embodiment, the cover material 214 can extend distally from the ring 216 to cover at least a portion of the hollow tube 212. As mentioned above, the hollow tube 212 can have features and functionality similar to that of hollow tube 12, 112 such as, but not limited to, a lumen through which surgical devices can pass and/or include a tapered portion or be tapered along the entirety of its length. In some embodiments, the hollow tube 212 can have a taper which can range from about 0.1 degrees to about 30 degrees, from about 1 degree to about 15 degrees, from about 3 degrees to about 10 degrees, about 5 degrees, or any other angle as desired. In some embodiments, the hollow tube 212 can have a taper less than about 15 degrees, less than about 10 degrees, less than about 5 degrees, or any other angle as desired.

As shown in the illustrated embodiment, an introducer catheter or dilator 219 can be slideable within the lumen of the tube 212. The system 210 can include a hub 218. As described above in connection with hub 118, the hub 218 can include features which facilitate manipulation of the hub 218 by an operator. As shown in the illustrated embodiment, the hub 218 can include a lumen through which devices can pass such as the dilator 219. The lumen can be positioned such that it is concentric with a lumen of the tube 212 and/or have a cross-sectional dimension which matches that of a lumen of the hollow tube 212.

As shown in the illustrated embodiment of FIG. 12, a proximal end 220 of the hollow tube 212, or a portion proximate the proximal end 220, can be attached directly to the hub 218 via any fasteners such as rivets, screws, bolts, sutures, clips or similar, via adhesives or similar, via welding the hollow tube 112 to the hub 118 or vice versa, any other mechanism or technique as desired, or a combination of such mechanisms and/or techniques. In some embodiments, the hollow tube 212 and the hub 218 can form an integral or monolithic unit. In some embodiments, the hollow tube 212 and the hub 218 can have a suspension and/or dampening element (not shown) placed between the tube 212 and the hub 218 similar to that described in connection with sealing system 110. In some embodiments, the suspension and/or dampening element can be placed between a proximal end 220 of the tube 212 and a distal end 222 of the hub 218. The hollow tube 212 and the hub 218 can be attached together via the suspension or dampening element. The suspension and/or dampening element can include those components discussed above in connection with FIG. 10.

As shown in the illustrated embodiment, the ring 216 can be sized and shaped such that it floats over the outer surface of the hollow tube 212. In some embodiments, the cover material 214 and/or the ring 216 can snugly fit over the outer surface of the hollow tube 212 such that the ring 216 is retained on the hollow tube 212 via a friction fit.

Similar to cover materials 14, 114 of sealing systems 10, 110, the cover material 214 can be formed from one or more of a number of bio-compatible materials. The properties of the bio-compatible materials can be chosen, for example, based on the application for the sealing system 210. For purposes of brevity, reference should be made to the discussion of materials and material properties for cover materials 14, 114 as said discussion also applies to cover material 214.

With continued reference to the embodiment of FIG. 12 which illustrates the sealing system 210, a distal end 224 of cover material 214 can be attached to a portion proximate a distal end 226 of the hollow tube 212. As shown in the illustrated embodiment, the cover material 214 is encapsulated within a portion of the hollow tube 212 proximate the distal end 226. This can be achieved, for example, by placing the distal end 224 of the cover material 214 over a portion of the hollow tube 212, placing a ring over the distal portion of the hollow tube 212 such that the ring contacts both the hollow tube 212 and the cover material 214, and melting or welding the ring over the hollow tube 212 and cover material 214 such that the ring couples the cover material 214 to the hollow tube 212. In some embodiments, the hollow tube 212 can have a slot through which the distal end 224 of the cover material 214 can be inserted. The hollow tube 212 can then be melted or welded over the distal end 224 of the cover material 214 to secure the distal end 224 to the hollow tube 212. In some embodiments, the cover material 214 can include a plurality of apertures proximate the distal end 224 such that, when the ring or hollow tube 212 is melted or welded, at least a portion of material can flow through the apertures of the cover material 214 to form a more secure attachment between the cover material 214 and the hollow tube 212.

In some embodiments, similar to cover materials 14, 114 of sealing systems 10, 110, the end of the cover material 214 can be inverted and extended into a lumen of the hollow tube 212 and attached to an internal surface at any position. Moreover, the cover material 214 can be attached at any other position along the external surface of the hollow tube 212. As with cover materials 14, 114, the cover material 214 can be attached to the hollow tube 212 via fasteners such as rivets, screws, bolts, sutures, clips or similar, via adhesives or similar, via welding the cover material 214 to the hollow tube 212 or vice versa, any other mechanism or technique as desired, or a combination of such mechanisms and/or techniques. For purposes of brevity, reference should be made to the discussion of the attachment of the cover material 114 to the hollow tube 112 as said discussion also applies to the attachment cover material 214 to hollow tube 212.

Similar to cover material 114 and ring 116 of sealing systems 110, the cover material 214 can be attached to the ring 216 at a variety of locations and can cover a variety of surfaces of the ring 216. The attachment can be chosen, for example, based on the application for the sealing system 210. For purposes of brevity, reference should be made to the discussion of the attachment of the cover material 114 to the ring 116 as said discussion also applies to the attachment cover material 214 to ring 216.

Similar to ring 116 of sealing system 110, the ring 216 can be formed from one or more of a number of bio-compatible materials and/or one or more components. The properties of the bio-compatible materials can be chosen, for example, based on the application for the sealing system 210. For purposes of brevity, reference should be made to the discussion of the construction, materials and material properties for ring 116 as said discussion also applies to ring 216.

Similar to sealing system 110, the sealing system 210 can be delivered percutaneously to the target site or can be used during an open or semi-open surgical procedure such as is the case during a transapical surgical approach. The steps of a procedure can follow that described in connection with the embodiment of FIGS. 11A-11C. Accordingly, for purposes of brevity, reference should be made to the discussion of those steps as said discussion applies to the sealing system 210.

With reference now to the embodiment of FIG. 13 which illustrates a sealing system 310, the sealing system 310 can be designed to seal an opening and/or puncture in an anatomical wall of a patient similar to that described in connection with the embodiments of FIGS. 1-12. The sealing system 310 can include components, such as tubular support or hollow tube 312, cover material or sealable material 314, button, ring or donut 316 and/or hub 318, having features and/or functionality similar to those described in connection with sealing systems 10, 110, 210 such as hollow tubes 12, 112, 212, cover materials 14, 114, 214, rings 116, 216 and/or hubs 118, 218. Accordingly, it should be understood that features and/or functionality of components of sealing systems 10, 110, 210 can also apply to components of sealing system 310.

With continued reference to the embodiment of FIG. 13 which illustrates the sealing system 310, the hollow tube 312 can support a bio-compatible cover material or sealable material 314 and an anchor assembly which can include a donut, ring or button 316, the anchor assembly being designed to retain the cover material 314 over the opening and/or puncture in the wall. As shown in the illustrated embodiment, the cover material 314 can extend distally from the ring 316 to cover at least a portion of the hollow tube 312. As mentioned above, the hollow tube 312 can have features and functionality similar to that of hollow tube 12, 112, 212 such as, but not limited to, a lumen through which surgical devices can pass and/or include a tapered portion. For example, as shown in the illustrated embodiment, an introducer catheter or dilator 319 can be slideable within the lumen of the tube 312. The system 310 can include a hub 318. As described above in connection with hubs 118, 218, the hub 318 can include features which facilitate manipulation of the hub 318 by an operator. As shown in the illustrated embodiment, the hub 318 can include a lumen through which devices can pass such as the dilator 319. The lumen can be positioned such that it is concentric with a lumen of the tube 312 and/or have a cross-sectional dimension which matches that of a lumen of the hollow tube 312.

As shown in the illustrated embodiment of FIG. 13, the hollow tube 312 and the hub 318 can be designed to be moveable relative to each other. For example, a proximal or receiver portion 320 of the hollow tube 312 can be loosely fitted over a distal portion 322 of the hub 318 such that the proximal portion 320 of the tube 312 floats over the distal or connector portion 322 of the hub 318. The proximal or receiver portion 320 of the hollow tube 312 can have a greater diameter than the remaining portion of the hollow tube 312 such that the distal or connector portion 322 can be received within the receiver portion 320. While the distal or connector portion 322 of the hub 318 is illustrated as having a length which enters only a portion of the hollow tube 312, it is contemplated that the distal or connector portion 322 can be of sufficient length to extend further into the hollow tube 312 such as up to the distal end 330 of the hollow tube 312. This can, for example, increase the stability between the hollow tube 312 and the hub 318 as the two components are moved relative to each other. In some embodiments, the proximal portion 320 of the hollow tube 312 can be coupled to the distal portion 322 of the hub 318 via a snap fit connector such as an annular protrusion on the hub 318 and an annular slot in the tube 312 or vice versa, a twist-lock such as a bayonet mount or threading, clips, adhesives, or similar mechanisms which can be releasable to allow the tube 312 and hub 318 to be moveable relative to each other. In some embodiments, the hollow tube 312 and the hub 318 can include mechanisms, such as a longitudinally oriented slots and protrusions or other types of mechanisms as desired, to prevent rotation of the tube 312 relative to the hub 318.

In some embodiments, the hollow tube 312 and the hub 318 can have a suspension and/or dampening element (not shown) which can be biased to separate the hollow tube 312 from the hub 318 similar to that described in connection with sealing systems 110, 210. For example, the suspension and/or dampening element can be placed between a proximal end of the tube 312 and the hub 318. The suspension and/or dampening element can include those components discussed in connection with FIG. 10. As will be described in further detail below, use of a suspension and/or dampening element, such as a spring element, can be designed to maintain tension of the cover material 314 as the hub 318 and hollow tube 312 is withdrawn away from the ring 316.

As shown in the illustrated embodiment, the ring 316 can be sized and shaped such that it floats over the outer surface of the hollow tube 312. The hollow tube 312 can include a one or more protrusions 324 against which the ring 316 can be placed. In some embodiments, the one or more protrusions 324 can be in the form of one or more spaced apart fingers that extend radially outwardly from the hollow tube. The one or more protrusions 324 can include three separate fingers which can be spaced apart approximately 120° from each other. Other shapes of protrusions 324 can also be used. Spacing between the one or more protrusions 324 can be advantageous during a surgical procedure as this can allow an operator to suture the ring 316 to the wall while the ring 316 is placed proximate or adjacent the one or more protrusions 324. In some embodiments, the one or more protrusions 324 can be a single annular flange.

The ring 316 can be secured to the one or more protrusions 324 via a connector 326. As shown in the illustrated embodiment, the connector 326 can be a suture although other types of connectors 326 can be used including, but not limited to, fasteners such as rivets, screws, bolts, clips or similar, via adhesives or similar, via welding the ring 316 to the one or more protrusions 324 or vice versa, any other mechanism or technique as desired, or a combination of such mechanisms and/or techniques. In some embodiments, the connector 326 can be added by the operator during the surgical procedure. In some embodiments, the cover material 314 and/or the ring 316 can snugly fit over the outer surface of the hollow tube 312 such that the ring 316 is retained on the hollow tube 312 via a friction fit.

Similar to cover materials 14, 114, 214 of sealing systems 10, 110, 210, the cover material 314 can be formed from one or more of a number of bio-compatible materials. The properties of the bio-compatible materials can be chosen, for example, based on the application for the sealing system 310. For purposes of brevity, reference should be made to the discussion of materials and material properties for cover materials 14, 114, 214 as said discussion also applies to cover material 314.

With continued reference to the embodiment of FIG. 13 which illustrates the sealing system 310, similar to cover materials 14 of sealing systems 10, the proximal end of the cover material 314 can be inverted and extended into the lumen of the hollow tube 312. A proximal end portion 328 of cover material 314 can then be attached to the hub 318. As shown in the illustrated embodiment, the cover material 314 can be attached to the distal portion 322 of the hub 318. In some embodiments, the end portion 328 can be attached to the hub 318 via welding, via an adhesive such as a polytetrafluoroethylene (PTFE) bond, or any other mechanism and/or technique as desired. For example, the end portion 328 can be attached to the hub 318 via fasteners such as rivets, screws, bolts, sutures, clips or any other fastener as desired.

Similar to cover materials 114, 214 and rings 116, 216 of sealing systems 110, 210, the cover material 314 can be attached to the ring 316 at a variety of locations and can cover a variety of surfaces of the ring 316. The attachment can be chosen, for example, based on the application for the sealing system 310. For purposes of brevity, reference should be made to the discussion of the attachment of the cover materials 114, 214 to the rings 116, 216 as said discussion also applies to the attachment cover material 314 to ring 316.

Moreover, similar to rings 116, 216 of sealing systems 110, 210 the ring 316 can be formed from one or more of a number of bio-compatible materials and/or one or more components. The properties of the bio-compatible materials can be chosen, for example, based on the application for the sealing system 310. For purposes of brevity, reference should be made to the discussion of the construction, materials and material properties for rings 116, 216 as said discussion also applies to ring 316.

Similar to sealing systems 110, 210, the sealing system 310 can be delivered percutaneously to the target site or can be used during an open or semi-open surgical procedure such as is the case during a transapical surgical approach. The steps of a procedure can roughly follow that described in connection with the embodiment of FIGS. 11A-11C. For purposes of brevity, those steps will be summarily described. Reference should be made to the discussion of those steps as said discussion applies to the sealing system 310.

During a first step, the operator can apply sutures between at least portions of the ring 316 and the anatomical wall of the patient while the ring 316 remains positioned some distance away from the anatomical wall. Accordingly, during this first step, suture lines can extend between the ring 316 and the anatomical wall. In some embodiments, such as those where the ring 316 is not coupled to one or more protrusions 324 of the hollow tube 312, the operator can couple the ring 316 to the one or more protrusions 324 via a connector 326. For example, the operator can suture the ring 316 to one or more of the protrusions 324 such that the ring 316 remains proximate or adjacent the protrusions 324. Of course, as noted above, the ring 316 can be coupled to one or more of the protrusions 324 via connectors 326 prior to the operation.

During a second step, in embodiments where the hollow tube 312 and the hub 318 are attached, the hollow tube can 312 be detached from hub 318 to allow the tube 312 and hub 318 to freely move relative to each other. The hollow tube 312 can be moved distally relative to the hub 318 in order to increase the tautness of the cover material 314 over the distal portion of the hollow tube 312. This can be facilitated via use of a suspension and/or dampening element, as described above, which can be biased to force the hollow tube 312 away from the hub 318 to maintain tautness in the cover material 314. For example, as the once the hollow tube 312 and the hub 318 are detached, the suspension and/or dampening element can apply a force upon the hollow tube 312 in a proximal direction relative to the hub 318 such that the cover material 314 remains taut.

During a third step, the hollow tube 312 can be inserted into an opening and/or puncture (not shown) in an anatomical wall of a patient. The hollow tube 312 can be moved in a distal direction towards the wall through the opening and/or puncture until the ring 316 is positioned at or proximate the wall. In some embodiments, such as those where the hollow tube 312 is introduced with a dilator 319, the dilator 319 can be used to form and/or expand the opening and/or puncture prior to entry by the hollow tube 312. After the hollow tube 312 has been placed into the opening and/or puncture with the ring 316 placed adjacent the anatomical wall, the sutures can then be tightened and knotted to secure the ring 316 in place adjacent the anatomical wall. With the hollow tube 312 placed within the opening and/or puncture, steps of another surgical procedure can be performed through the hub 318 and the hollow tube 312 during this stage. Upon completion of this other surgical procedure, the ring 316 can be removed from the one or more protrusions 324 to allow the ring 316 to freely move relative to the hollow tube 312 and hub 318. This can be achieved, in some embodiments, by severing the connector 326.

During a fourth step, the hub 318 can then be moved or retracted proximally away from the wall. As the hub 318 is retracted proximally away from the wall, the ring 316 can move distal relative to the hollow tube 312 due to the cover material 314 being attached to the hub 318. As the hub 318 is retracted proximally away from the wall, the hollow tube 312 should also be moved or retracted proximally away from the wall in order to maintain tautness in the cover material 314. As shown in the illustrated embodiment, since the cover material 314 is attached to the hub 318 and wraps over the distal end 330 of the tube 312, the hollow tube 312 should be generally retracted at a speed approximately half of that of the hub 318 in order to maintain tautness in the cover material 314. This can be facilitated via use of a suspension and/or dampening element, as described above, which can be biased to force the hollow tube 312 away from the hub 318 to maintain tautness in the cover material 314. For example, as the operator proximally retracts the hub 318 away from the opening and/or puncture, the suspension and/or dampening element can apply a force upon the hollow tube 312 in the proximal direction whereas the cover material 314 can apply a force upon the hollow tube 312 in the distal direction. Accordingly, as the hub 318 is retracted from the wall, the suspension and/or dampening element can cause the hollow tube 312 to be retracted at approximately half the speed of the hub 318.

During a fifth step, once the tube 312 has reached a sufficiently proximal position relative to the ring 316, a substantial portion, if not substantially the entirety, of the cover material 314 can now be inside-out, at which point the tube 312 may be removed completely, leaving behind the ring 316 and the cover material 314. The cover material 314 can then be severed proximal the ring 316 and tied off using sutures or other devices and techniques such as those described herein. For example, the cover material 314 can be tied off using a fitting or clip, similar to fitting or clip 32, and/or tied off using staples, or other fasteners, adhesives or similar, welding or similar techniques, any other device or technique as desired, or a combination of such mechanisms and/or techniques.

With reference now to the embodiment of FIGS. 16A and 16B which illustrates a perspective view and a side view sealing system 510 respectively, the sealing system 510 can be designed to seal an opening and/or puncture in an anatomical wall of a patient similar to that described in connection with the embodiments of FIGS. 1-13. The sealing system 510 can include components, such as tubular support or hollow tube 512, cover material or sealable material 514, button, ring or donut 516 and/or hub 518, having features and/or functionality similar to those described in connection with sealing systems 10, 110, 210, 310 such as hollow tubes 12, 112, 212, 312 cover materials 14, 114, 214, 314, rings 116, 216, 316 and/or hubs 118, 218, 318. Accordingly, it should be understood that features and/or functionality of components of sealing systems 10, 110, 210, 310 can also apply to components of sealing system 510.

Figure 16A:
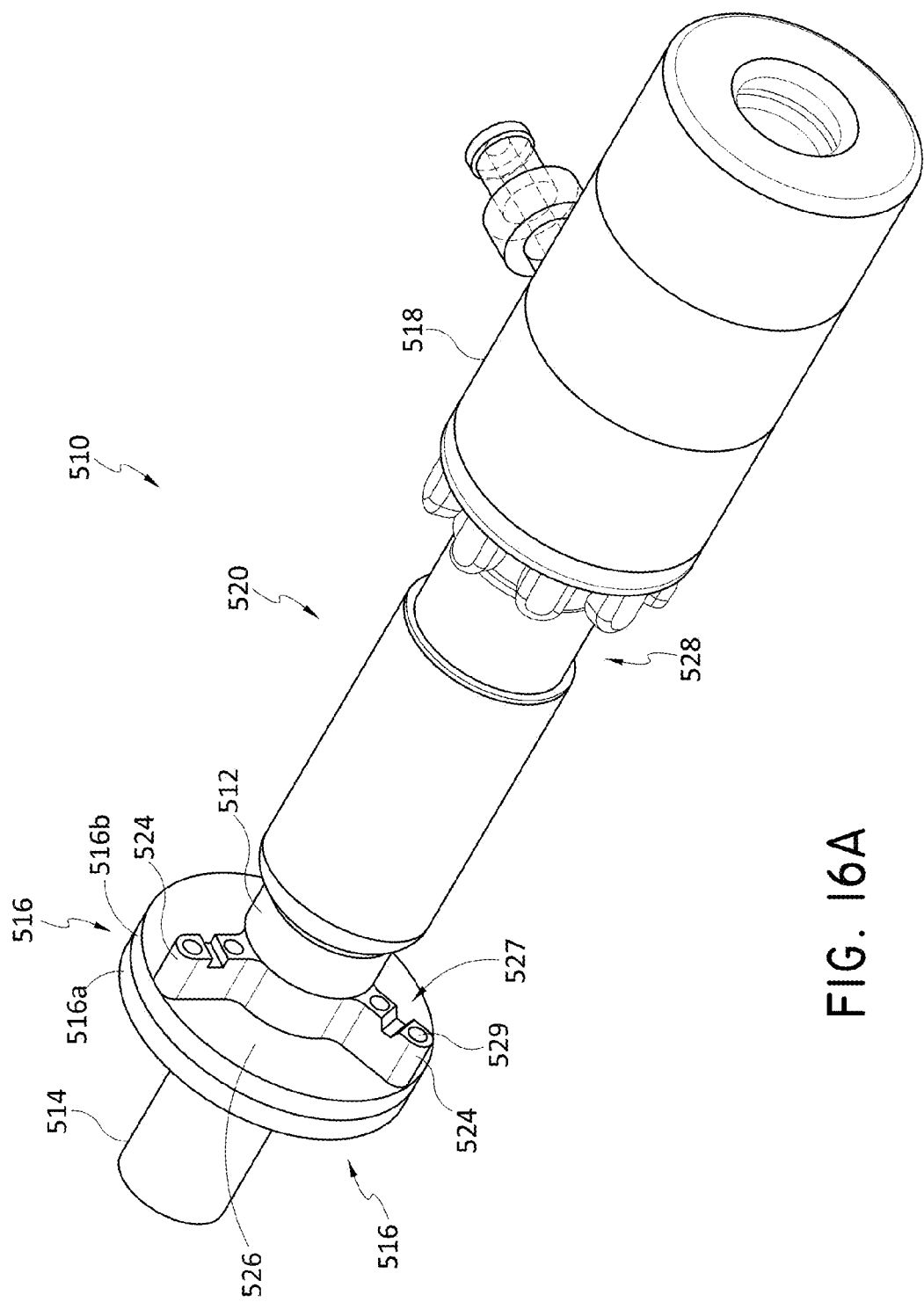
FIG. 16A shows a perspective view of another embodiment of a sealing system having a hollow tube, a cover material, a ring and a hub, the hollow tube having a one or more protrusions.
Figure 16B:
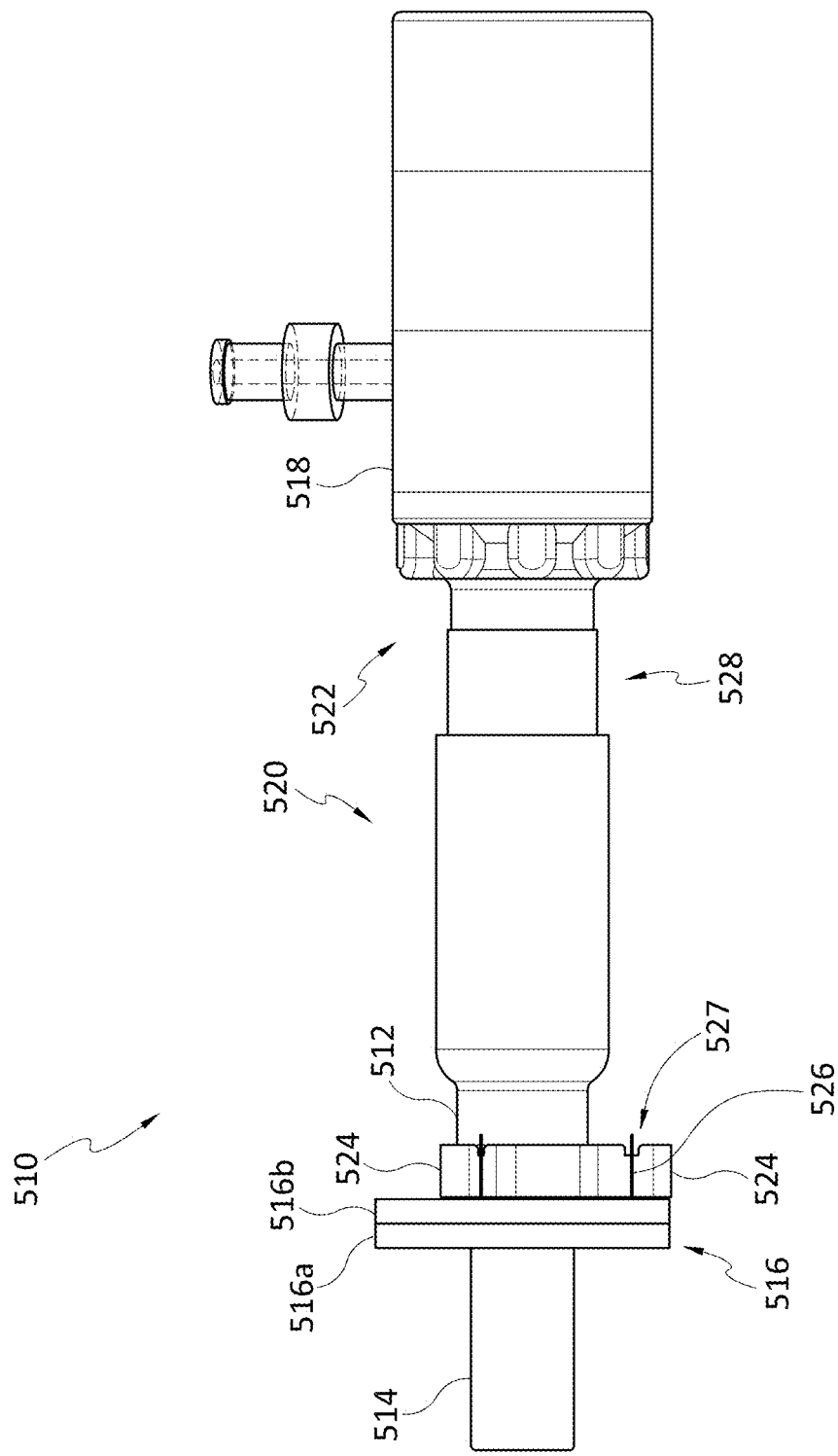
FIG. 16B shows a side view of the sealing system of FIG. 16A

With continued reference to the embodiment of FIGS. 16A and 16B which illustrates the sealing system 510, the hollow tube 512 can support a bio-compatible cover material or sealable material 514 and an anchor assembly which can include a donut or ring 516, the anchor assembly being designed to retain the cover material 514 over the opening and/or puncture in the wall. As shown in the illustrated embodiment, the cover material 514 can extend distally from the ring 516 to cover at least a portion of the hollow tube 512. As mentioned above, the hollow tube 512 can have features and functionality similar to that of hollow tube 12, 112, 212, 312 such as, but not limited to, a lumen through which surgical devices can pass and/or include a tapered portion. In some embodiments such as illustrated, the hollow tube 512 can have multiple dimensions, such as a first smaller dimension distal to the ring 516 and larger, stepped-up dimensions proximal to the ring 516. As illustrated, the tube 512 may have a relatively larger proximal portion 520 compared to the portion of the tube 512 that supports the cover 514 distal to the ring 516. The tube 512 may be formed from a single tube or multiple tubes joined together. The system 510 can include a hub 518. As described above in connection with hubs 118, 218, 318, the hub 518 can include features which facilitate manipulation of the hub 518 by an operator. As shown in the illustrated embodiment, the hub 518 can include a lumen through which devices can pass. The lumen can be positioned such that it is concentric with a lumen of the tube 512 and/or have a cross-sectional dimension which matches that of a lumen of the hollow tube 512.

As shown in the illustrated embodiment of FIGS. 16A and 16B, the hollow tube 512 and the hub 518 can be designed to be moveable relative to each other similar to that described in connection with hollow tube 312 and hub 318 of sealing system 310. For purposes of brevity, reference should be made to the discussion of the moveable relationship between hollow tube 312 and hub 318 as said discussion also applies to hollow tube 512 and hub 518.

In some embodiments, the hollow tube 512 and the hub 518 can have a suspension and/or dampening element (not shown) which can be biased to separate the hollow tube 512 from the hub 518 similar to that described in connection with sealing systems 110, 210, 310. For example, the suspension and/or dampening element can be placed between a proximal end of the tube 512 and the hub 518. The suspension and/or dampening element can include those components discussed in connection with FIG. 10. Similar to that described above in connection with hollow tube 312, cover material 314 and hub 318, use of a suspension and/or dampening element, such as a spring element, can be designed to maintain tension of the cover material 514 as the hub 518 and hollow tube 512 is withdrawn away from the ring 516.

As shown in the illustrated embodiment, the ring 516 can be sized and shaped such that it floats over the outer surface of the hollow tube 512. The hollow tube 512 can include a one or more protrusions 524, similar to protrusions 324, against which the ring 516 can be placed. In some embodiments, the one or more protrusions 524 can be in the form of one or more spaced apart fingers. For example, as shown in the illustrated embodiment, the one or more protrusions 524 can include three separate fingers which can be spaced apart approximately 120° from each other. Other shapes of protrusions 524 can also be used. In some embodiments, the one or more protrusions 524 can be a single annular flange.

The ring 516 can be secured to the one or more protrusions 524 via a connector (shown generally at location 526 in FIG. 16A, and illustrated more expressly in FIG. 16B). As shown in the illustrated embodiment, the connector 526 can be a suture although other types of connectors 526 can be used including, but not limited to, fasteners such as rivets, screws, bolts, clips or similar, via adhesives or similar, via welding the ring 516 to the one or more protrusions 524 or vice versa, any other mechanism or technique as desired, or a combination of such mechanisms and/or techniques. As shown in the illustrated embodiment, the one or more protrusions 524 can include features which facilitate use of connectors 526. Such features can include slots 527, apertures 529, and/or any other feature through or onto which connectors 526, such as sutures, can be received. As noted above, in some embodiments, the connectors 526 can be added by the operator during the surgical procedure. The existence of such slots 527 and/or apertures 529 can facilitate coupling and/or removal of the ring 516 from the one or more protrusions 524 during a surgical procedure. For example, sutures can pass through the apertures 529 when coupling the ring 516 to the one or more protrusions 524. During removal, the slot 527 can provide additional space between the suture and the one or more protrusions 524 to facilitate severing of the suture. In some embodiments, the cover material 514 and/or the ring 516 can snugly fit over the outer surface of the hollow tube 512 such that the ring 516 is retained on the hollow tube 512 via a friction fit.

Similar to cover materials 14, 114, 214, 314 of sealing systems 10, 110, 210, 310, the cover material 514 can be formed from one or more of a number of bio-compatible materials. The properties of the bio-compatible materials can be chosen, for example, based on the application for the sealing system 510. For purposes of brevity, reference should be made to the discussion of materials and material properties for cover materials 14, 114, 214, 314 as said discussion also applies to cover material 514.

With continued reference to the embodiment of FIGS. 16A and 16B, which illustrates the sealing system 510, similar to cover materials 14, 314 of sealing systems 10, 310, the proximal end 528 of the cover material 514 can be inverted and extended into the lumen of the hollow tube 512 before the system is placed into a patient. A proximal end portion 528 of cover material 514 can then be attached to the hub 518. As shown in the illustrated embodiment, the cover material 514 can be attached to the distal portion 522 of the hub 518. In some embodiments, the end portion 528 can be attached to the hub 518 via welding, via an adhesive such as a polytetrafluoroethylene (PTFE) bond, or any other mechanism and/or technique as desired. For example, the end portion 528 can be attached to the hub 518 via fasteners such as rivets, screws, bolts, sutures, clips or any other fastener as desired.

Similar to cover materials 114, 214, 314 and rings 116, 216, 316 of sealing systems 110, 210, 310, the cover material 514 can be attached to the ring 516 at a variety of locations and can cover a variety of surfaces of the ring 516. The attachment can be chosen, for example, based on the application for the sealing system 510. For purposes of brevity, reference should be made to the discussion of the attachment of the cover materials 114, 214, 314 to the rings 116, 216, 316 as said discussion also applies to the attachment cover material 514 to ring 516.

Moreover, similar to rings 116, 216, 316 of sealing systems 110, 210, 310 the ring 516 can be formed from one or more of a number of bio-compatible materials and/or one or more components. For example, as shown in the illustrated embodiment, the ring 516 is formed from a distal ring-shaped component 516a and a proximal ring-shaped component 516b, with a portion of the cover material 514 placed therebetween. The properties of the bio-compatible materials can be chosen, for example, based on the application for the sealing system 510. For purposes of brevity, reference should be made to the discussion of the construction, materials and material properties for rings 116, 216, 316 as said discussion also applies to ring 516.

Similar to sealing systems 110, 210, 310 the sealing system 510 can be delivered percutaneously to the target site or can be used during an open or semi-open surgical procedure such as is the case during a transapical surgical approach. The steps of a procedure can roughly follow that described in connection with the embodiment of FIGS. 11A-11C and FIG. 13. Reference should be made to the discussion of those steps as said discussion applies to the sealing system 510.

Figure 14A:
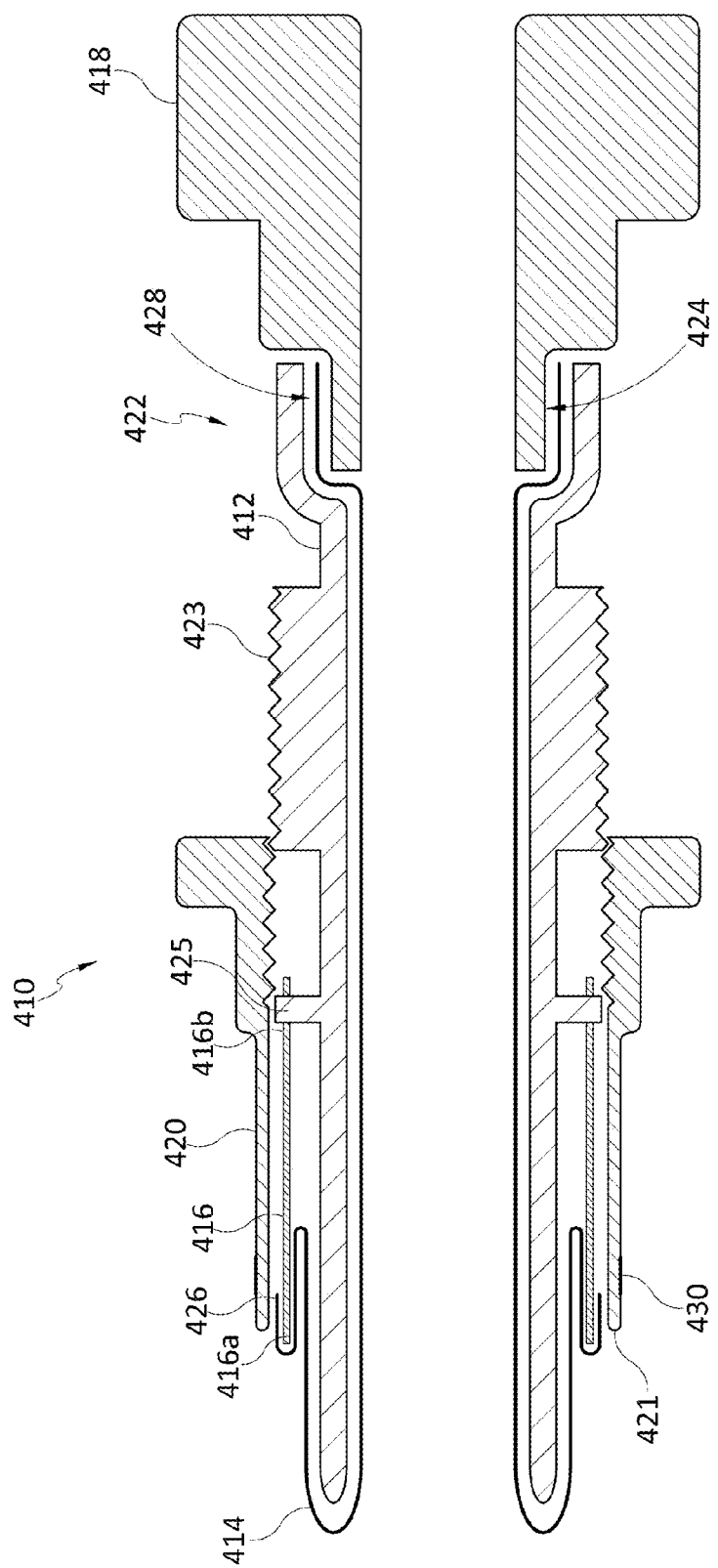
FIG. 14A shows a cross-sectional, schematic view of an embodiment of a sealing system having a hollow tube, a cover material, a C-clip anchor, a hub and a sheath, the C-clip anchor being in a delivery position.
Figure 14B:
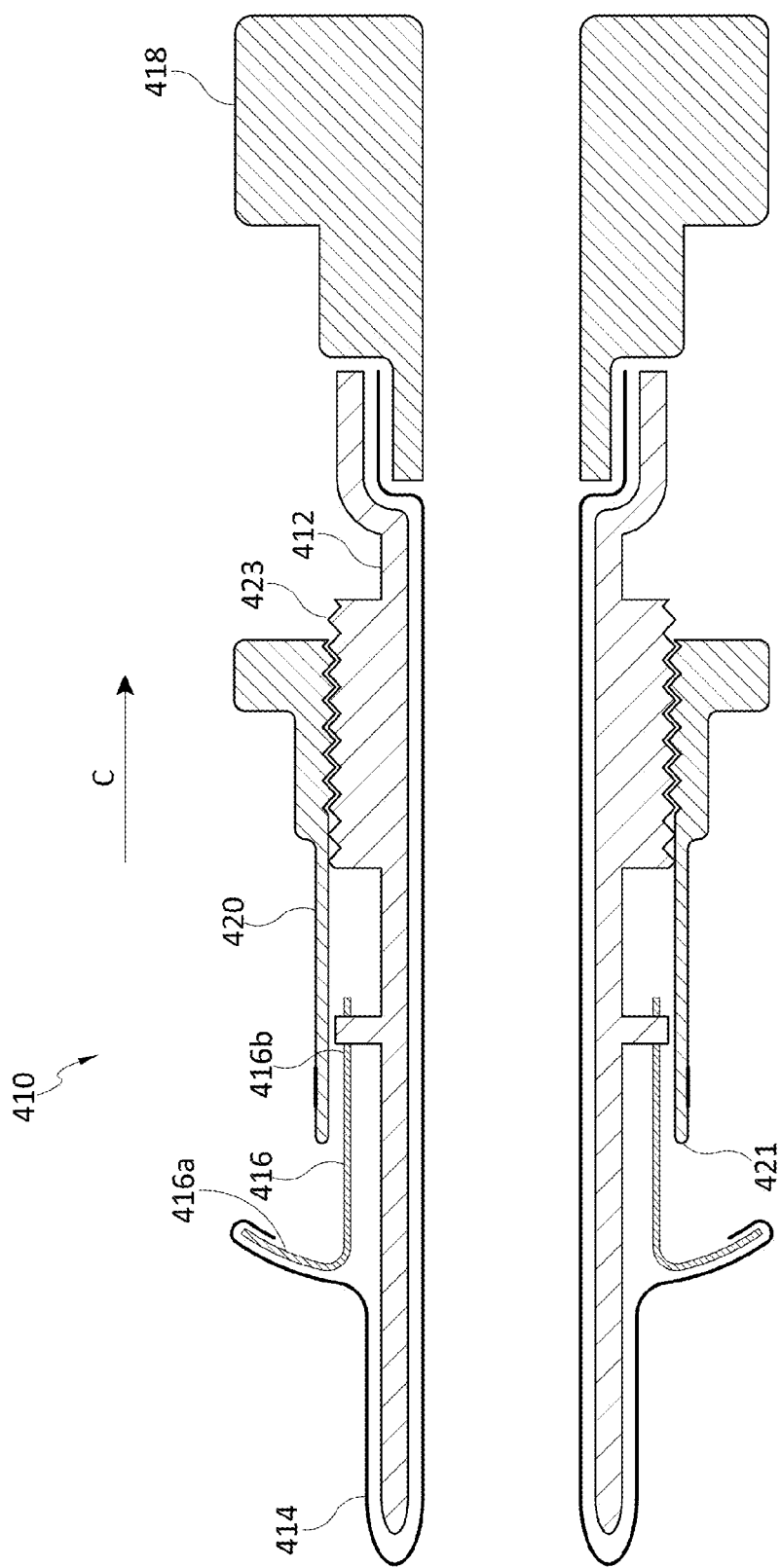
FIG. 14B shows a schematic view of the sealing system of FIG. 14A with the C-clip anchor being in a partially deployed position.
Figure 15:
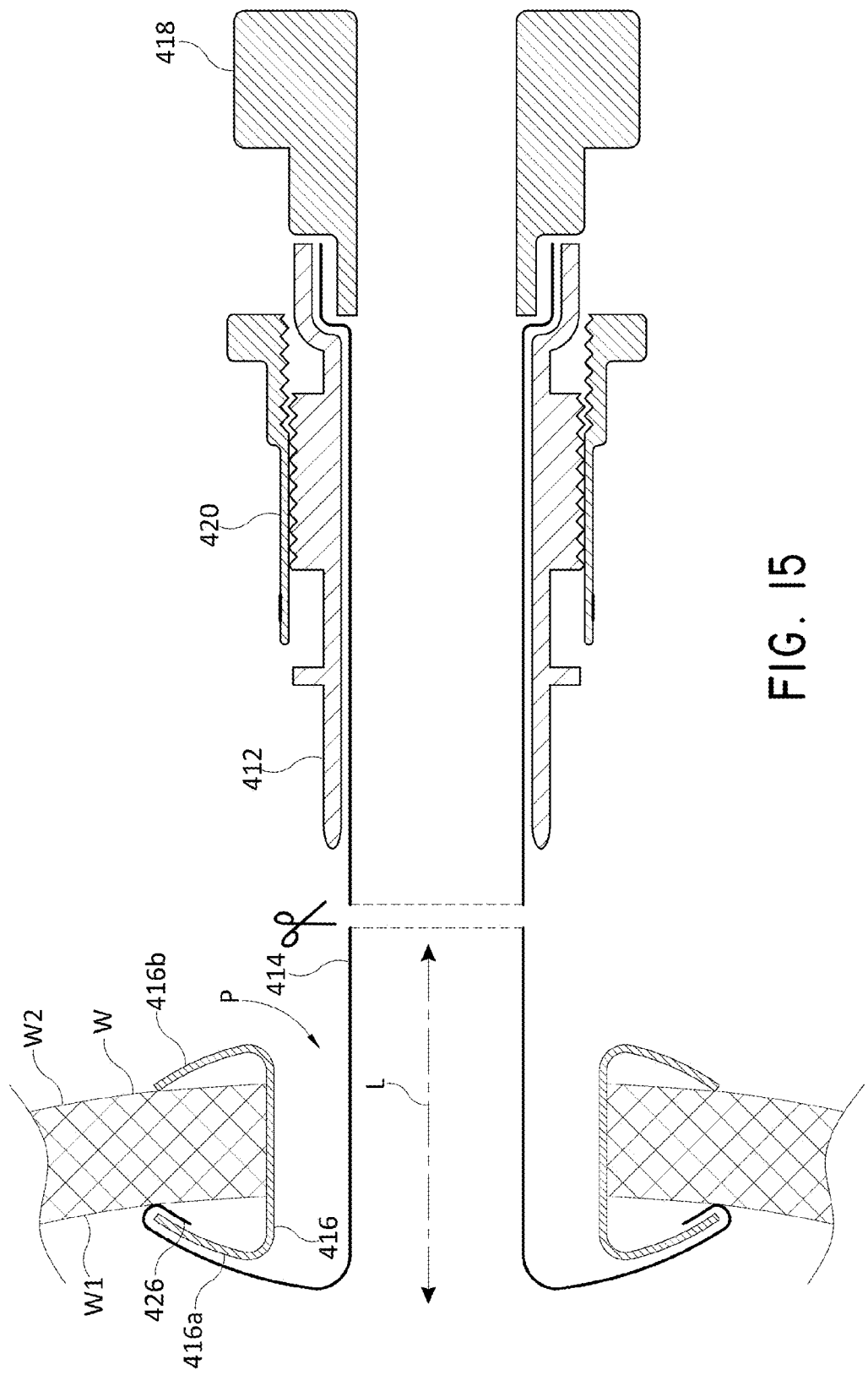
FIG. 15 shows a schematic view of the sealing system of FIG. 14A with the C-clip anchor deployed in an opening of an anatomical wall.

With reference now to the embodiment of FIGS. 14A-14C and 15 which illustrates a sealing system 410, the sealing system 410 can be designed to seal an opening and/or puncture P in an anatomical wall W (as shown in FIG. 15) of a patient similar to that described in connection with the embodiments of FIGS. 1-13, 16A and 16B. The sealing system 410 can include components, such as tubular support or hollow tube 412, cover material or sealable material 414, C-clip anchor 416 and/or hub 418, having features and/or functionality similar to those described in connection with sealing systems 10, 110, 210, 310 such as hollow tubes 12, 112, 212, 312, cover materials 14, 114, 214, 314, anchors 16 and/or hubs 118, 218, 318. Accordingly, it should be understood that features and/or functionality of components of sealing systems 10, 110, 210, 310 can also apply to components of sealing system 410.

With continued reference to the embodiment of FIGS. 14A-14C and 15 which illustrates the sealing system 410, the hollow tube 412 can support a bio-compatible cover material or sealable material 414 and an anchor assembly which can include C-clip anchor 416, the anchor assembly being designed to retain the cover material 414 over the opening and/or puncture P in the wall W. As shown in the illustrated embodiment, the cover material 414 can extend distally from the C-clip anchor 416 to cover at least a portion of the hollow tube 412. As mentioned above, the hollow tube 412 can have features and functionality similar to that of hollow tube 12, 112, 212, 312 such as, but not limited to, a lumen through which surgical devices can pass and/or include a tapered portion (not shown). As described above in connection with hubs 118, 218, 318, the hub 418 can include features which facilitate manipulation of the hub 418 by an operator. As shown in the illustrated embodiment, the hub 418 can include a lumen through which devices can pass. The lumen can be positioned such that it is concentric with a lumen of the tube 412 and/or have a cross-sectional dimension which matches that of a lumen of the hollow tube 412.

As shown in the illustrated embodiment of FIGS. 14A-14C and 15, a sheath 420 can be positioned around the hollow tube 412 and the C-clip anchor 416 to retain the anchor in a first, delivery position. As shown in the illustrated embodiment, in a first, delivery position, a distal portion 421 of the sheath 420 can be positioned proximate the distal anchor 416a. In some embodiments, the distal portion 421 can extend over the distal anchor 416a and/or be tapered radially inwardly to facilitate the placement of the sheath 420 within the opening and/or puncture P in the wall W. As will be described in further detail below, the sheath 420 can be moveable relative to the hollow tube 412 to uncover and deploy the C-clip anchor 416. The sheath 420 can be coupled to the hollow tube 412 via a connector 423 such as threading. Threading can be advantageous as it can allow an operator to more precisely control the movement of the sheath 420 relative to the hollow tube 412. This precision can be altered based on characteristics of the threading, such as the pitch. Other types of connectors 423 can also be used such as ratchets. In some embodiments, the connector 423 is designed such that it maintains the positioning of the sheath 420 relative to the hollow tube 412 when at rest. In some embodiments, movement of the sheath 420 relative to the hollow tube 412 can occur via use of an electromechanical device, such as a linear actuator.

As shown in the illustrated embodiment, in order to prevent or reduce the likelihood that the C-clip anchor 416 is rotated as a result of rotation of the sheath 420 relative to the hollow tube 412, the hollow tube can include one or more prongs or radial extensions 425 which can define notches or slots into which portions of the C-clip anchor 416 can be placed. The prongs or radial extensions 425 can be placed proximate portions of the C-clip anchor 416 to keep the C-clip anchor 416 aligned rotationally with respect to the hollow tube 412. In some embodiments, the prongs or radial extensions 425 can also attach to the C-clip anchor 416. As shown, the prongs or radial extensions 425 can be placed proximate to and/or attach to one or more proximal anchors 416b of the C-clip anchor 416a. The prongs or radial extensions 425 can also be placed proximate to and/or attach to one or more distal anchors 416a and/or some other portion of the C-clip anchor 416. The prongs or radial extensions 425 can be designed such that they do not inhibit the C-clip anchor 416 from transitioning from the first, delivery position to the second, deployed position.

As shown in the illustrated embodiment of FIGS. 14A-14C and 15, the hollow tube 412 and the hub 418 can be designed to be moveable relative to each other in a similar manner to that described in connection with hollow tube 312 and hub 318. For example, as shown, a proximal or receiver portion 422 of the hollow tube 412 can be loosely fitted over a distal or connector portion 424 of the hub 418 such that the proximal or connector portion 422 of the tube 412 floats over the distal or receiver portion 424 of the hub 418. In some embodiments, the proximal or receiver portion 422 of the hollow tube 412 can be attached to the distal or connector portion 424 of the hub 418 via a snap fit connector such as an annular protrusion on the hub 418 and an annular slot in the tube 412 or vice versa, a twist-lock such as a bayonet mount or threading, clips, adhesives, or similar mechanisms which can be releasable to allow the tube 412 and hub 418 to be moveable relative to each other. In some embodiments, the hollow tube 412 and the hub 418 can include mechanisms, such as a longitudinally oriented slots and protrusions or other types of mechanisms as desired, to prevent rotation of the tube 412 relative to the hub 418. This can be particularly advantageous when threading is used as connector 423 since this can allow the operator to grasp the hub 418 and rotate the sheath 420 without also rotating the tube 412. In some embodiments, the hollow tube 412 can be fixedly attached to the hub 418.

In some embodiments, the hollow tube 412 and the hub 418 can have a suspension and/or dampening element (not shown) which can be biased to separate the hollow tube 412 from the hub 418 similar to that described in connection with sealing systems 110, 210, 310. For example, the suspension and/or element can be placed between a proximal end of the tube 412 and the hub 418. The suspension and/or dampening element can include those components discussed in connection with the suspension and/or dampening elements of FIG. 10. As discussed in connection with the embodiment of FIG. 13, use of a suspension and/or dampening element, such as a spring element, can help maintain tension of the cover material 414 as the hub 418 is withdrawn.

With continued reference to the embodiment of FIGS. 14A-14C and 15, the C-clip anchor 416 can include a plurality of distal anchors 416a and a plurality of proximal anchors 416b. The distal and/or proximal anchors 416a, 416b can be made of flexible material, preferably a shape-memory material such as nitinol or other shape-memory metal or polymer, that permits a first, delivery position (as shown in FIG. 14A) and a second, deployed position or wall engagement position (as shown in FIGS. 14C and 15). As shown in the embodiment of FIG. 14A, in the first, delivery position, the distal and proximal anchors 416a, 416b are movable towards the hollow tube 412 for delivery to and positioning at a target site. As shown in the embodiment of FIGS. 14C and 15, in the second, deployed position, the distal and proximal anchors 416a, 416b are movable outwardly away from the hollow tube 412 to engage the surrounding tissue at the target site.

In some embodiments, the C-clip anchor 416 can have a single unitary configuration with a plurality of distal anchors 416a and proximal anchors 416b attached together via a frame (not shown). The frame can have a wireframe construction and expand radially outward or contract radially inward relative to a longitudinal axis L of the C-clip anchor 416 upon deployment of the C-clip anchor 416 at the target site. Expansion of the frame upon deployment can further enhance the seal between the cover material 414, C-clip anchor 416, and the tissue of wall W since more pressure can be exerted on the tissue. Of course, depending on the application, such as if the tissue of the wall W can expand such that the opening and/or puncture P is of a smaller size, it may be advantageous to instead have the frame contract radially inward to reduce the radial dimension of the C-clip anchor 416.

In some embodiments, the C-clip anchor 416 can be formed from a plurality of discrete anchors secured together. For example, in some embodiments, one or more distal anchors 416a and one or more proximal anchors 416b can form a discrete unit which can then be secured together to form the C-clip anchor 416. In some embodiments, one or more distal anchors form a discrete unit and one or more proximal anchors form a discrete unit which can then be secured together to form the C-clip anchor 416.

As shown in the embodiment of FIGS. 14A-14C and 15, an end portion 426 of cover material 414 can be attached to an outwardly facing surface of one or more distal anchors 416a when the distal anchors 416a are in the first, delivery position such that, when the distal anchors 416a are in the second, deployed position and contact a distal side W1, such as an internal surface, of wall W, the end portion 426 of the cover material 414 is placed in direct contact with the wall W and positioned between the distal anchor 416a and the internal surface of wall W. In some embodiments, an end portion 426 of cover material 414 can be attached to an outwardly facing surface of one or more proximal anchors 416b when the proximal anchors 416b are in the first, delivery position such that, when the proximal anchors 416b are in the second, deployed position and contact a proximal side W2, such as an external surface, of wall W, the end portion 426 of the cover material 414 is placed in direct contact with the wall W and positioned between the proximal anchor 416a and the internal surface of wall W. Of course, the end portion 426 of the cover material 414 can be attached to any other outwardly facing surface of the C-clip anchor 416 including a central portion between the distal and proximal anchors 416a, 416b. It should be understood that that end portion 426 of the cover material 414 can be attached to inwardly facing surfaces of the distal and/or proximal anchors 416a, 416b when the distal and/or proximal anchors 416a, 416b are in the first, delivery position.

In some embodiments, the cover material 414 can be positioned such that it covers some portion of the outwardly facing surface of the C-clip anchor 416 when the C-clip anchors 416 is in the first, delivery position. In this manner, the cover material 414 can serve as an external liner for the C-clip anchor 416. In some embodiments, this can be a portion of the distal or proximal anchors 416a, 416b to which the cover material 414 is attached. In some embodiments, the cover material 414 can cover a substantial portion, if not the entirety, of the outwardly facing surface of the C-clip anchor 416 when the C-clip anchor 416 is in the first, delivery position. For example, with reference to the embodiment of FIG. 14A, the end portion 426 can be extended across the outwardly facing surface from the distal anchor 416a to the proximal anchor 416b and attached to the proximal anchor 416b. In such an embodiment, the cover material 414 would thus cover outwardly facing surfaces of the distal anchor 416a and a central portion of the C-clip anchor 416 as well as a portion of the outwardly facing surfaces of the proximal anchor 417. This can potentially provide some advantages by increasing the total surface area of the cover material 414 in contact with the anatomical wall W. Depending on the application, this can enhance the sealing effect of the C-clip anchor 416 and cover material 414. Moreover, in some embodiments, one or more of the distal and/or proximal anchors 416a, 416b to which the cover material 414 is attached can be longer than the other anchors 416a, 416b to maintain tension in the cover material 414 after the C-clip anchor 416 is in the second, deployed position.

In some embodiments, the cover material 414 can be positioned such that it covers some portion of the inwardly facing surface of the C-clip anchor 416 when the C-clip anchor 416 is in the first, delivery position. In this manner, the cover material 414 can serve as an internal liner for the C-clip anchor 416. In some embodiments, this can be a portion of the distal or proximal anchors 416a, 416b to which the cover material 414 is attached. In some embodiments, the cover material 414 can cover a substantial portion, if not the entirety, of the inwardly facing surface of the C-clip anchor 416 when the C-clip anchor 416 is in the first, delivery position.

With continued reference to the embodiment of FIGS. 14A-14C and 15, similar to cover materials 14, 314 of sealing systems 10, 310, a proximal end of the cover material 414 can be inverted and extended into the lumen of the hollow tube 412. A proximal end portion 428 of cover material 414 can then be attached to the hub 418. As shown in the illustrated embodiment, the cover material 414 can be attached to the distal portion 422 of the hub 418. In some embodiments, the end portion 428 can be attached to the hub 418 via welding, via an adhesive such as a polytetrafluoroethylene (PTFE) bond, or any other mechanism and/or technique as desired. For example, the end portion 428 can be attached to the hub 418 via fasteners such as rivets, screws, bolts, sutures, clips or any other fastener as desired.

Similar to cover materials 14, 114, 214, 314 of sealing systems 10, 110, 210, 310, the cover material 414 can be formed from one or more of a number of bio-compatible materials. The properties of the bio-compatible materials can be chosen, for example, based on the application for the sealing system 410. For purposes of brevity, reference should be made to the discussion of materials and material properties for cover materials 14, 114, 214, 314 as said discussion also applies to cover material 414.

With continued reference to the embodiments of FIGS. 14A-14C and 15, steps in the deployment of the sealing system 410 are now described. The sealing system 410 can be delivered percutaneously to the target site or can be used during an open or semi-open surgical procedure such as is the case during a transapical surgical approach. With reference first to the embodiment of FIG. 14A, the hollow tube 412 and the sheath 420 can be inserted into an opening and/or puncture P in an anatomical wall W (as shown in FIG. 15) of a patient. The hollow tube 412 and sheath 420 can be moved in a distal direction towards the wall W through the opening and/or puncture until the C-clip anchor 416 is properly positioned at the target site. Proper positioning of the C-clip anchor 416 can be facilitated by use of one or more marker bands 430 positioned on the sheath 420. These marker bands 430 can signal to the operator the position of the C-clip anchor 416 relative to the sheath 420. For example, as shown in the illustrated embodiment, the marker band 420 can indicate the position of the distal anchors 416a. The marker bands 430 can be designed to interact with surgical imaging tools to further facilitate positioning of the C-clip anchor 416 prior to deployment.

With reference next to the embodiment of FIG. 14B, the sheath 420 can be retracted proximally relative to the hollow tube 412, as shown by arrow C, until the distal anchors 416a are uncovered. As shown in the illustrated embodiment with connectors 423 in the form of threads, this can be achieved by rotating the sheath 420 relative to the hollow tube 412. In embodiments where the distal anchors 416a are biased in the second, deployed position, the distal anchors 416a can automatically spring towards the second, deployed position. As shown in the illustrated embodiment, the distal anchors 416a rotate to this second, deployed position. The distal anchors 416a can then engage the distal side or internal surface W1 of the anatomical wall W (as shown in FIG. 15). In some embodiments, the hollow tube 416a can be pulled in a proximal direction to ensure that the distal anchors 416a have engaged the distal side W1 of the anatomical wall W.

With reference next to the embodiment of FIG. 14C, the sheath 420 can be retracted further proximally relative to the hollow tube 412, as shown by arrow D, until the proximal anchors 416b are uncovered. In embodiments where the proximal anchors 416b are biased in the second, deployed position, the proximal anchors 416b can automatically spring towards the second, deployed position. As shown in the illustrated embodiment, the proximal anchors 416b rotate to this second, deployed position. The proximal anchors 416b can then engage the proximal side W2 of the anatomical wall W (as shown in FIG. 15). During this stage, with the hollow tube 412 still placed within the opening and/or puncture, steps of another surgical procedure can be performed through the hub 418 and the hollow tube 412.

With reference next to the embodiment of FIG. 15, the hollow tube 412 can be moved or retracted proximally relative to the C-clip anchor 416. Once the tube 412 has reached a sufficiently proximal position relative to the C-clip anchor 416, the tube 412 may be removed completely, leaving behind the C-clip anchor 416 and the cover material 414. As shown in the embodiment of FIG. 15, the cover material 414 can be severed proximal the C-clip anchor 416. In some embodiments, a fitting or clip, similar to clip 32 as described in connection with the embodiment of FIG. 2 can be used to seal the end of the cover material 414. In some embodiments, the cover material 414 can be tied off using sutures, staples or other fasteners, adhesives or similar, welding or similar techniques, any other device or technique as desired, or a combination of such mechanisms and/or techniques. As shown in the illustrated embodiment, the cover material 414 can be severed by cutting the cover material 414. In some embodiments, the attachment between the cover material 414 and the hub 418 can be severed by pulling the hollow tube 418 proximal relative to the cover material 414.

In some embodiments, the sealing systems, such as sealing systems 10, 110, 210, 310, 410, 510, can be used for other types of surgical procedures or integrated into other surgical devices. For example, the sealing systems can be integrated with a ventricular assist device (VAD) such as a left ventricular assist device (LVAD). A VAD can be used to partially assist or completely replace the function of a failing heart. For example, an LVAD can be used to pump blood from the left ventricle to the aorta. Accordingly, the LVAD can include a pumping device which pumps fluid received from an inlet opening of a fluid inlet tube to an outlet in the aorta, the fluid inlet tube being inserted into the left ventricle.

Components of the sealing systems can be integrated with the LVAD. For example, the hollow tubes 12, 112, 212, 312, 412, 512 can be used as the fluid inlet tube of the LVAD with cover materials 14, 114, 214, 314, 414, 514 and anchor assemblies such as anchors 16, rings 116, 216, 316, 516, or C-clip anchor 416 configured as described above in connection with FIGS. 1-16B. The steps of the procedures for sealing an opening can be performed when the inlet tube of the LVAD is removed. Advantageously, the cover material and anchor assembly can be used to form a seal while the fluid inlet tube is inserted into the heart and can later be used to seal the opening and/or puncture when the fluid inlet outlet tube is removed.

In some embodiments, the sealing systems, such as sealing systems 10, 110, 210, 310, 410, 510, can be used with an intracatheter pump apparatus. For example, the intracatheter pump apparatus can be sized to extend through a transapical opening, into the left ventricle, and into the aorta such that the intracatheter pump apparatus can assist with the pumping of blood from the left ventricle to the aorta. In some embodiments, the intracatheter pump apparatus can include a pumping device which pumps fluid received from an inlet opening of a fluid inlet tube to an outlet opening of a fluid outlet tube, the fluid inlet tube being positioned within the left ventricle and the fluid outlet tube being positioned within the aorta. In some embodiments, the inlet opening and the outlet opening can be positioned on the same tube with the pumping device positioned within the tube and between the inlet and outlet openings. One example of an intracatheter pump apparatus is the Impella® 2.5 available from Abiomed. Such an apparatus includes an elongate catheter, a pump motor near the distal end of the catheter, an outlet area distal to the pump motor, and a blood inlet area distal to the outlet area. When such an apparatus is used in the procedure as described above, the inlet area and the outlet area would be switched, with the outlet being distal to the inlet, and with the pump configured to pump fluid from the inlet to the outlet.

Components of the sealing systems can be integrated with the intracatheter pump apparatus. For example, the distal end of the cover materials 14, 114, 214, 314, 414, 514 can be attached to the intracatheter pump apparatus with the proximal end attached to the anchor assembly such as anchors 16, rings 116, 216, 316, 516, or C-clip anchor 416. The distal end of the cover material can be attached to the intracathether pump apparatus at a position proximal of the inlet and outlet openings of the fluid inlet and outlet tubes respectively. Accordingly, when the intracatheter pump apparatus is introduced transapically into the heart via an opening and/or puncture and positioned within the heart, the anchor assembly and the cover material can form a seal to prevent the outflow of fluids from the opening and/or puncture. Advantageously, the cover material and anchor assembly can be used to form a seal while the intracatheter pump apparatus is positioned with the heart and can later be used to seal the opening and/or puncture when the intracatheter pump apparatus is removed.

As described above, the cover material, such as cover materials 14, 114, 214, 314, 414, 514, can be tied off upon severing of the cover material from the hollow tube using a variety of devices and techniques including sutures, staples, adhesives and the like. In some embodiments, the cover material can be tied off and severed simultaneously. For example, the cover material can be cut and stapled simultaneously, reducing the potential for complications.

In some embodiments, the cover material can be tied off using a spring. The spring can have an outer edge and define an interior opening or area having an expandable cross-sectional area. In some embodiments, the spring can be a conical or spiral spring. In some embodiments, portions of the spring or the entirety of the spring can be flat such as a flat spiral spring. The spring can be biased such that, when the cover material is placed through the interior opening, the spring can exert a sufficient force upon the cover material to seal the cover material around the interior opening. In one embodiment, the spring may comprise either a flat or conical coil or spiral spring which comprises an outer edge having a fixed dimension and an expandable interior opening. When a structure such as a hollow tube is placed through the interior opening, the interior opening will expand, and when the structure is removed, the interior opening will compress. In embodiments where the spring is a flat spring, when a structure is placed through the interior opening, the spring may assume a conical shape. In some embodiments, the conical shape of the spring may have a distal end configured to be attached to a proximal end of the anchor assembly and a proximal end, wherein the distal end is larger than the proximal end. As a structure such as the hollow tube is removed from the interior opening, this may cause the conical shape of the spring to transition to a flattened or a relatively more flattened configuration.

In some embodiments, the outer edge of the spring can be coupled to a proximal end of the anchor assembly, such as anchors 16, rings 116, 216, 316, 516, or C-clip anchor 416. During the initial stages of a procedure where the anchor assembly is positioned over a hollow tube, the spring can be coupled to the proximal end of the anchor assembly the interior opening can be expanded to fit over the hollow tube. As the hollow tube is retracted proximally with respect to the anchor assembly and the spring, the spring slides distally over the hollow tube. As the hollow tube is further retracted proximally relative to the anchor assembly and the spring, the spring can slide over the distal end of the hollow tube and onto the cover material which has been inverted as a result of the proximal retraction of the hollow tube. Due to the biasing of the interior opening of the spring towards a reduced cross-sectional area, the interior opening can exert a sufficient force on the cover material to seal the cover material proximal of the anchor assembly. In some embodiments, the spring can continue to slide over the cover material as the hollow tube is further retracted proximally. The cover material can be severed proximal of the spring.

In some embodiments, the cover material can be tied off using a purse string or similar approach. In some embodiments, the cover material can be provided with a purse-string suture and/or an annular sleeve portion through which the purse string can be positioned. The purse string can be initially positioned along an interior and/or exterior surface of the cover material and can be positioned distal of the anchor assembly. For example, the purse string can be positioned along an interior surface distal of the anchor assembly prior to inversion of the cover material such that, after inversion, the purse string is then positioned on an exterior surface proximal of the anchor assembly. In this manner, the purse string can advantageously provide a more secure seal upon tightening. The purse string can have free ends which can be pulled to tighten the purse string around the cover material thereby tying off the cover material. This can occur automatically by attaching the free ends to the hollow tube such that, as the anchor assembly is moved distal relative to the hollow tube, the free ends are pulled and tighten the cover material. Of course, the free ends can be manually tightened by having the operator pull the free ends.

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that such features, elements and/or steps are in any way required for one or more embodiments.

Moreover, the following terminology may have been used herein. The singular forms "a," "an," and "the" include plural referents unless the context clearly dictates otherwise. Thus, for example, reference to an item includes reference to one or more of such items. The term "ones" refers to one, two, or more, and generally applies to the selection of some or all of a quantity. The term "about," "approximately," or "similar" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. A method of sealing openings within an anatomical wall, the method comprising:
   delivering percutaneously a puncture seal closure system within a sheath to an opening in an anatomical wall to be sealed, where the system comprises an elongate tubular support having a distal end and a proximal end, the tubular support configured for percutaneous delivery to the opening to be sealed; a cover of bio-compatible material configured to cover at least a portion of the tubular support from at least the distal end of the tubular support to a central portion of the tubular support, the cover material having a distal end configured to engage the distal end of the tubular support and a proximal end, the cover further comprising an anchor covering portion positioned proximate the proximal end of the cover; and an anchor assembly comprising a plurality of distal anchors and a plurality of proximal anchors positioned proximal the central portion of the tubular support, the distal and proximal anchors sufficiently malleable and configured to be foldable against the tubular support when in a first delivery position, and to foldable radially outwardly away from the tubular support in a second wall engagement position;
   positioning the puncture seal system in-situ within the opening so that the distal anchors are positioned along the distal side of the opening wall and the proximal anchors are positioned along the proximal side of the opening wall;
   withdrawing the sheath to permit the anchors positioned in the wall engagement position to secure the seal system in place;
   removing the tubular support in a proximal direction so as to draw the cover material inside-out from a distal-most position to a proximal-most position;
   severing the exposed end of the cover material with a closure member for closing off an end of the cover material after removal of the tubular support wherein the opening is sealed using the anchor covering portion of the cover material in combination with the anchors.

2. A system for sealing an opening within an anatomical wall, the system comprising:
   an elongate tubular support having a proximal end and a distal end, the tubular support configured for delivery into the opening to be sealed;
   an anchor assembly configured to be secured to the anatomical wall adjacent the opening, wherein the elongate tubular support is positionable in a first position within the anchor assembly wherein the proximal end of the tubular support is proximal to the anchor assembly and the distal end of the tubular support is distal to the anchor assembly; and
   a cover of bio-compatible material connected to the anchor assembly and configured to extend distally from the anchor assembly to cover at least a portion of the tubular support when the tubular support is in the first position;
   wherein the tubular support is moveable from the first position to a second position, wherein in the second position the distal end of the tubular support is proximal to the anchor assembly, and movement of the tubular support from the first position to the second position draws the cover material inside-out such that the cover material extends proximally from the anchor assembly; and wherein when the tubular support is in its first position, the cover extends to the distal end of the tubular support and is then inverted to extend within a lumen of the tubular support.

3. The system of claim 2, wherein the anchor assembly comprises a plurality of proximal anchors and a plurality of distal anchors, the proximal and distal anchors being foldable towards the tubular support in a first delivery position and being expandable radially outwardly away from the tubular support in a second wall engagement position.

4. The system of claim 3, wherein the cover is connected to the distal anchors.

5. The system of claim 3, wherein the cover is connected to the proximal anchors.

6. The system of claim 2, wherein the anchor assembly comprises a C-clip.

7. The system of claim 2, wherein the anchor assembly comprises a button or ring that is securable adjacent an opening in the anatomical wall.

8. The system of claim 2, wherein the cover is connected to the tubular support at or proximate the distal end of the tubular support.

9. The system of claim 2, wherein the cover is connected to the tubular support at or proximate the proximal end of the tubular support within the lumen.

10. A method of sealing an opening within an anatomical wall, the method comprising:
providing a sealing system comprising an elongate tubular support having a proximal end and a distal end, an anchor assembly provided over the elongate tubular support positioned between the proximal and distal ends, and a cover of bio-compatible material connected to the anchor assembly and extending distally therefrom to cover at least a portion of the tubular support;
positioning the tubular support within the opening within the anatomical wall such that the proximal end of the tubular support is proximal of the opening and the distal end of the tubular support is distal of the opening, wherein the cover covering at least a portion of the tubular support extends at least distally of the opening;
securing the anchor assembly to the anatomical wall adjacent the opening;
moving the tubular support in a proximal direction so as to draw the cover material inside-out from a distal-most position wherein the cover extends at least distally of the opening to a proximal-most position wherein the cover extends proximally of the opening; and
sealing a portion of the cover extending proximally of the opening.

11. The method of claim 10, further comprising severing a portion of the cover extending proximally of the opening.

12. The method of claim 10, wherein the opening within the anatomical wall is formed by delivering the sealing system through the anatomical wall.

13. The method of claim 12, wherein delivering the sealing system further comprises delivering a dilator through the anatomical wall simultaneously with the tubular support.

14. The method of claim 10, wherein securing the anchor assembly to the anatomical wall comprises expanding anchors on proximal and distal sides of the anatomical wall.

15. The method of claim 10, wherein securing the anchor assembly comprising suturing the anchor assembly to a proximal surface of the anatomical wall adjacent the opening.

16. The method of claim 10, wherein the opening is an opening in the heart.

17. The method of claim 10, further comprising performing a procedure in the heart using one or more instruments delivered through a central lumen of the tubular support after securing the anchor assembly to the anatomical wall adjacent the opening and before moving the tubular support in a proximal direction so as to draw the cover material inside-out from a distal-most position wherein the cover extends at least distally of the opening to a proximal-most position wherein the cover extends proximally of the opening.

* * * * *

UNITED STATES PATENT AND TRADEMARK OFFICE
CERTIFICATE OF CORRECTION

PATENT NO. : 9,724,083 B2
APPLICATION NO. : 14/341693
DATED : August 8, 2017
INVENTOR(S) : Quadri et al.

It is certified that error appears in the above-identified patent and that said Letters Patent is hereby corrected as shown below:

In the Specification

Column 4, Line 55, delete "transpical" and insert -- transapical --.

Column 29, Line 37, delete "intracathether" and insert -- intracatheter --.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*